United States Patent [19]

Erlanger et al.

[11] Patent Number: 5,144,010

[45] Date of Patent: Sep. 1, 1992

[54] METHOD OF PRODUCING MONOCLONAL AUTO-ANTI-IDIOTYPIC ANTIBODIES

[75] Inventors: Bernard F. Erlanger, Whitestone; William L. Cleveland, New York, both of N.Y.

[73] Assignee: The Trustees of Columbia University in the City of New York, New York, N.Y.

[21] Appl. No.: 273,654

[22] Filed: Nov. 18, 1989

Related U.S. Application Data

[63] Continuation of Ser. No. 767,516, Aug. 20, 1985, abandoned, which is a continuation-in-part of Ser. No. 644,550, Aug. 27, 1984, abandoned.

[51] Int. Cl.⁵ .......................... C07K 15/28; C12N 5/16
[52] U.S. Cl. .............. 530/387.2; 435/240.27; 530/809; 530/388.22; 530/388.9
[58] Field of Search ............ 435/68, 172.2, 240.27, 435/949; 935/90, 104, 107; 436/548, 800; 530/387, 806, 807, 809

[56] References Cited

U.S. PATENT DOCUMENTS

| | | | |
|---|---|---|---|
| 4,513,088 | 4/1985 | Levy et al. | 435/172.2 |
| 4,536,479 | 8/1985 | Vander-Mallie | 436/800 |
| 4,545,986 | 10/1985 | Malley | 435/68 |
| 4,661,444 | 4/1987 | Li | 436/800 |
| 4,661,586 | 4/1987 | Levy et al. | 435/948 |

OTHER PUBLICATIONS

Ukena et al., "Effects of Several 5'-Carboxamide Derivatives of Adenosine on Adenosine Receptors of Human Platelets and Rat Fat Cells," Biological Abstracts, vol. 79(8), #70621.

Ku, "Monoclonal Antibodies to Adenosine Receptor by an Auto-Anti-Idiotypic Approach", Chem. Abs., vol. 111, #151679.

Ku et al., "Monoclonal Antibodies to Adenosine Receptor by an Auto-Anti-Idiotypic Approach", J. Immun., vol. 139, 2376-2384, 1987.

Cleveland et al., Nature 305 pp. 56-57 (1983).

Erlanger et al., Monoclonal and Anti-Idiotypic Antibodies pp. 163-176 (1984) Alan R. Liss Inc., NY.

Stohrer et al., Journal of Immunology 131(3) pp. 1375-1379 (1983).

Hatzubai et al., Journal of Immunology 126(6) pp. 2397-2402 (1981).

Frackelton et al., Journal of Biological Chemistry 255(11) pp. 5286-5290 (1980).

Shechter et al., Science 216 pp. 542-545 (1982).

Goidl et al., Journal of Experimental Medicine 150 pp. 154-165 (1979).

Wassermann et al., Proc. Natl. Acad. Sci. USA 79 pp. 4810-4814 (1982).

Nowinski et al., Science 210 pp. 537-539 (1980).

*Primary Examiner*—John Doll
*Assistant Examiner*—George C. Elliott
*Attorney, Agent, or Firm*—John P. White; Craig J. Arnold

[57] ABSTRACT

This invention provides an auto-anti-idiotypic method for producing a monoclonal anti-idiotypic antibody. The method involves contacting lymphoid cells of an animal under suitable conditions with an effective antibody-raising amount of an antigen, collecting the lymphoid cells from the animal at a suitable time after the contacting and fusing the collected lymphoid cells with appropriate myeloma cells to produce a series of hybridoma cells each of which produces a monoclonal antibody. The method further involves screening, under suitable conditions, the series of hybridoma cells so produced to identify those which secrete a monoclonal antibody capable of binding to an antibody directed to the antigen, or to a receptor where the antigen is a ligand to the receptor, separately culturing a hybridoma cell so identified in an appropriate medium, and separately recovering under suitable conditions the monoclonal anti-idiotypic antibody produced by the hybridoma cell.

1 Claim, 13 Drawing Sheets

Figure 2

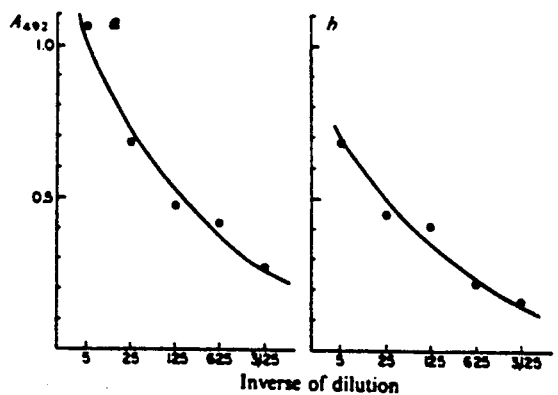

Inverse of dilution

Fig. 1 Binding of *Torpedo* AChR (*a*) and rabbit anti-BisQ (*b*) by F8-D5. Wells of polystyrene plates (Corning) were coated with 150 μl of either 400 ng ml$^{-1}$ purified rabbit anti-BisQ[1] in 0.1 M NaHCO$_3$, pH 9.3 or 3 μg ml$^{-1}$ purified *Torpedo* receptor in the same buffer. Coating was accomplished by incubating for 2 h at 37 °C. After two washings with 0.01 M phosphate buffer-0.14 M NaCl, pH 7.2, containing 0.05% Tween-20 (PBS-Tween), the wells were exposed to the various concentrations of F8-D5 in PBS-Tween. After incubation at 37 °C for 2 h, the wells were washed three times with PBS-Tween and then filled with 200 μl of 1:1,000 dilution in PBS-Tween of goat anti-mouse immunoglobulin labelled with horseradish peroxidase (Sigma). After incubation at 37 °C for 1 h, the wells were washed three times with PBS-Tween. Peroxidase was assayed by incubation with *o*-phenylenediamine dihydrochloride (7 mg in 10 ml 0.1 M citrate-phosphate buffer, pH 4.8, containing 5 μl of 30% H$_2$O$_2$) for 10 min. The reaction was stopped with 50 μl per well of 4 M H$_2$SO$_4$, and the colour read at 492 nm in a Multiskan Titertek apparatus. Values have been corrected for a PBS blank which was never higher than 0.150. The above conditions were not chosen for optimal sensitivity but for speed and convenience.

METHOD OF PRODUCING MONOCLONAL AUTO-ANTI-IDIOTYPIC ANTIBODIES

The invention described herein was made with Government support under grant numbers NS-15581, NS-17904, AI-17949 and T32-AI-07161 from the National Institutes of Health, United States Department of Health and Human Services. The Government has certain rights in the invention.

This application is a continuation of U.S. Ser. No. 767,516, filed Aug. 20, 1985, now abandoned, which is a continuation-in-part of U.S. Ser. No. 644,550, filed Aug. 27, 1984, now abandoned the contents of which are hereby incorporated by reference into the present application.

BACKGROUND OF THE INVENTION

Portions of the information set forth herein have been published. See W. L. Cleveland et al., Nature 306(5929):56-57 (1983). Within this application several publications are referenced by arabic numerals within parentheses. Full citations for these references may be found at the end of the specification immediately preceding the claims. The disclosures of these publications in their entireties are hereby incorporated by reference into this application in order to more fully describe the state of the art to which this invention pertains.

This invention concerns a method for the direct production of monoclonal anti-idiotypic antibodies, preferably ones that mimic receptors or ligands of receptors. A receptor is defined herein as a molecular structure that interacts with another structure, referred to as a ligand, as part of a biological process. Receptors can include, but are not restricted to, enzymes, immunoglobulins, lymphokines, cell surface molecules, attachment sites on viruses and cells, specific binding proteins such as those which bind nucleic acids, hormone binding molecules and metal-binding molecules such as calmodulin. A ligand is similarly defined as a structure that reacts with a receptor as defined above. In addition to binding to a receptor, a ligand as defined herein may act as an agonist or as an antagonist with respect to the receptor.

Antibodies arise when an animal is immunized with a particular antigen. The variable regions of such antibodies contain a set of antigenic determinants known as the idiotype which is usually associated with antigen specificity. Anti-idiotypic antibodies may arise when an animal is injected with specific idiotypic antibody molecules which have been previously obtained and purified. In such an experiment the animal immunized with the idiotypic antibody produces antibodies directed against the idiotypic determinants of the injected antibody. The idiotypic antibodies may then bind to either the antigen or the anti-idiotypic antibodies so produced. Regardless of functional differences, macromolecules having the same binding specificities can also show homologies at their binding sites. Thus immunizing an animal with purified idiotypic antibodies raised against an antigen which is a ligand for a biological receptor may raise anti-idiotypic antibodies which bind to both the idiotypic antibodies and the receptor for the ligand (1).

Anti-idiotype antibodies thus afford one route to functional anti-receptor antibodies, which have been implicated in several auto-immune diseases. At least some of these diseases (1,2) might originate from an antiidiotypic response to antibodies formed against biologically active ligands normally present in vivo, such as insulin or thyrotropin. The likelihood of an antiidiotypic etiology increases if the patients' antibodies are found to be directed at the combining site of a receptor Although not always the case (3), this has been found to be true in many patients with myasthenia gravis (4), particularly in those who are severely ill. Moreover, it has been shown (1) that experimental myasthenia gravis can be induced in rabbits via the antiidiotypic route. Thus, an aberrant anti-idiotypic response could have a role in at least some cases of myasthenia gravis in humans. In Graves disease, the specificity of circulating anti-thyroid receptor antibodies is usually directed at the combining site of the thyrotropin receptor (5). These anti-thyroid receptor antibodies are therefore probably anti-idiotypic, directed at idiotypes of anti-thyrotropin antibody.

Adenosine receptors are also important for several reasons. They are involved in the regulation of blood flow in arteries and arterioles, in particular in the heart. Thus, they are one of the many factors involved in determining blood circulation in this organ. They are also involved in the modulation of nervous impulses and, generally speaking, tend, when activated, to have a calming effect on animals. There is good evidence that these receptors are the targets for caffeine, which seems to reverse the action of adenosine and produce agitation, rather than tranquility. Finally, there is recent evidence that alcoholism may very well be associated with abnormalities in the adenosine receptor.

Previous methods for the production and study of anti-receptor antibodies required immunizing animals with purified receptors in order to raise the desired anti-bodies (6,7,8).

Recently (1), a procedure was described for preparing antibodies to the acetylcholine receptor (AChR) based on immunoglobulin idiotypes and on the above-mentioned hypothesis that, regardless of functional differences, macromolecules of the same specificity will show structural homologies in their binding sites. Antibodies were prepared in rabbits to a structurally constrained agonist of AChR, trans-3,3'-bis( -trimethylammonium) azotoluene bromide (BisQ) (9,10). These antibodies mimicked the binding specificity of AChR in its activated state (11) i.e., agonists were bound with affinities that were in accord with their biological activities while antagonists were bound poorly. Rabbits were then immunized with a specifically purified preparation of anti-BisQ antibodies to elicit a population of antiidiotypic antibodies specific for the binding sites of anti-BisQ. A portion of the anti-idiotypic antibodies (12,13) produced in the second set of rabbits crossreacted with determinants on AChR preparations from *Torpedo californica, Electrophorus electricus* and rat muscle. Moreover, several of the rabbits showed signs of experimental myasthenia gravis, in which circulating AChR antibodies are typically found.

Anti-idiotypic antibodies against the thyrotropin receptor have also been reported (14). In that experiment, thyrotropin (TSH) specific antibodies (idiotypic) raised in rats were injected into rabbits which then produced the anti-idiotypic antibodies against the rat anti-TSH antibodies.

It has been postulated that the anti-idiotypic response plays a role in regulating the immune response (12,13,15). According to this theory, injection of an antigen elicits, in addition to antibodies to the antigen, other populations that include anti-idiotypic antibodies directed at the combining sites of the antigen-specific antibodies. If the antigen-specific antibodies recognize a ligand of a receptor, then the antiidiotypic antibodies should bind receptor.

In the past, the spontaneous generation of anti-idiotypes in response to immunization against an antigen has seldom been detected (2). Recently however, the spontaneous appearance of auto-anti-idiotypic antibody was observed during a normal human immune response to tetanus toxoid (16). Similarly, immunization with insulin was observed to cause the spontaneous appearance of insulin receptor-specific antibodies (2).

The difficulty in detecting the anti-idiotypic response results from the low titres of circulating anti-idiotypic antibodies formed (1,2) and to the observation that the cellular events giving rise to the anti-idiotypic response are only ,a transient phenomenon. Attempts to utilize the auto-anti-idiotypic response to produce anti-idiotypic antibodies would also involve technical problems that arise from the formation of immune complexes, an important limitation of serological studies.

The present invention surprisingly overcomes the aforementioned limitations by providing a novel method for producing anti-idiotype antibodies which depends on the use of hybridoma technology to immortalize the cells which produce the anti-idiotype antibodies. By immortalizing and cloning the cells active at the time of cell harvest, the cellular events are "frozen" in time, making it possible to produce and study clones and large quantities of their products that may have only a transient existence in vivo. Moreover, since the immortalized clones are separated from each other, this approach avoids the technical problems that arise from the formation of immune complexes. It should be understood that the method of this invention eliminates the need to obtain a purified idiotypic antibody in order to produce the anti-idiotypic antibody and the need to obtain a purified receptor in order to produce an antireceptor antibody.

In view of the low efficiency usually observed for cell fusion (about one antibody-producing cell in one thousand is immortalized), combined with the low titres of naturally occurring anti-idiotypic antibodies and the possibility that the low titres may well have resulted from suppression of the very cells that produce such antibodies, it should further be understood that the success of this auto-anti-idiotypic method is indeed an unexpected and surprising result.

SUMMARY OF THE INVENTION

This invention concerns a method for producing a monoclonal anti-idiotypic antibody, preferably one that binds to a receptor or ligand, and more preferably, one that mimics a receptor or ligand. The method is an auto-anti-idiotypic method which involves the following steps:

(a) contacting lymphoid cells, e.g. spleen cells, of an animal under suitable conditions with an effective antibody-raising amount of an antigen;

(b) collecting the lymphoid cells from the animal at a suitable time after the contacting;

(c) fusing the collected lymphoid cells with appropriate myeloma cells to produce a series of hybridoma cells each of which produces a monoclonal antibody;

(d) screening under suitable conditions the series of hybridoma cells so produced to identify those which secrete a monoclonal antibody capable of binding to an antibody directed to an antigen and to a receptor of the antigen;

(e) separately culturing a hybridoma cell so identified in an appropriate medium, e.g. in vitro or in a suitable animal;

(f) separately recovering under suitable conditions the monoclonal anti-idiotypic antibody produced by the hybridoma cell; and (g) identifying the subpopulations of anti-idiotypic antibodies that react with receptors.

Suitable antigens include among others a synthetic or naturally occurring molecule capable of binding to a receptor such as an adenosine receptor; acetylcholine receptor (AChR); steroid receptor, e.g. an estrogen, androgen or glucocorticoid receptor; thyroid stimulating hormone (TSH, thyrotropin) receptor; insulin receptor; $\beta$-adrenergic receptor; dopamine receptor, one of the chemotactic receptors of the neutrophil or other receptors as previously defined. When such an antigen is used, the anti-idiotypic monoclonal antibody is capable of binding to the respective receptor.

The antigen can be conjugated to a protein such as keyhole limpet hemocyanin, thyroglobulin or a serum protein, e.g. bovine or rabbit serum albumin.

The receptor of interest can be an adenosine receptor and the antigen the molecule $N^6$-carboxypentamethylene adenosine which is conjugated to a protein such as bovine serum albumin, rabbit serum albumin or keyhole limpet hemocyanin.

The receptor of interest can also be an acetylcholine receptor, and the antigen the molecule BisQ which is conjugated to a protein such as bovine serum albumin, rabbit serum albumin or keyhole limpet hemocyanin.

An animal is suitably immunized by a conventional method, e.g. by intraperitoneal, intramuscular, intradermal or other mode of injection with a solution containing the antigen and preferably a suitable adjuvant. Preferably the injection is repeated with a suitable booster injection after about two to about four weeks, e.g. after about three weeks.

A suitable time for collecting lymphoid, e.g. spleen cells from the injected animal is at least about three days after the injection, preferably after a booster injection.

Alternately, lymphoid cells may be cultured in virrto in the presence of the antigen to effect antibody production (26). Again, the lymphoid cells may be collected at least about three days after contact and immunization with the antigen.

Hybridoma cells produced by fusing the lymphoid cells and appropriate myeloma cells are screened by immunoassay, preferably an enzyme immunoassay, of the hybridoma culture medium against an immobilized antibody to the antigen and a labeled antibody capable both of binding to the monoclonal anti-idiotypic antibody under appropriate conditions and of being detected.

The hybridoma cells are screened by immunoassay of the hybridoma culture medium against immobilized receptor and a labeled antibody capable both of binding to the monoclonal anti-idiotypic antibody under appropriate conditions and of being detected.

The hybridoma cells may be separately cultured by conventional methods in an appropriate medium. The appropriate medium may be an in vitro cell culture or a suitable animal host.

Thus, by the method of this invention a monoclonal anti-idiotypic antibody, and in a preferred embodiment one capable of binding to a receptor under suitable conditions, may be produced without the necessity of immunizing the animal with either a previously identified, recovered and purified idiotypic antibody to the antigen or a previously identified, recovered and purified receptor capable of binding the antigen as a ligand.

By this method a monoclonal anti-idiotypic antibody may be produced which is capable of binding to a receptor such as an adenosine receptor or an acetylcholine receptor or another receptor as defined above. In an especially preferred embodiment the antibody of this invention acts as an agonist or antagonist of the receptor.

BRIEF DESCRIPTION OF THE FIGURES

FIG. 2. Illustrates the binding of Torpedo AChR (a) and rabbit anti-BisQ (b) by F8-D5 monoclonal anti-idiotypic antibody.

DETAILED DESCRIPTION OF THE INVENTION

Figure 1:
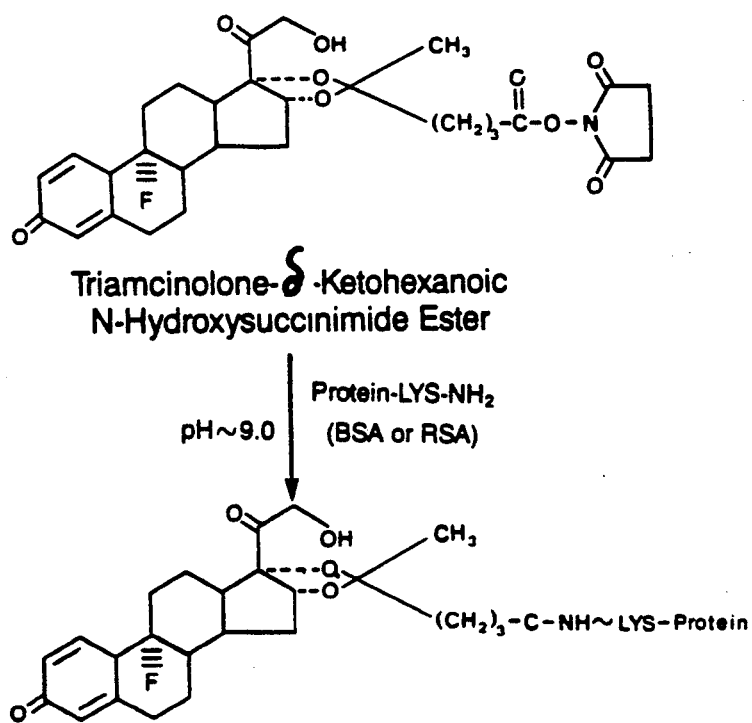
FIG. 1. Illustrates schematically the synthetic route used to prepare the triamcinolone protein conjugate.

As indicated above, this invention provides a method for producing a monoclonal anti-idiotypic antibody which involves:

(a) contacting lymphoid cells of an animal under suitable conditions with an effective antibody-raising amount of an antigen, (b) collecting the lymphoid cells at a suitable time after the contacting, (c) fusing the collected lymphoid cells with appropriate myeloma cells to produce a series of hybridoma cells each of which produces a monoclonal antibody, (d) screening under suitable conditions the series of hybridoma cells so produced to identify those which secrete a monoclonal antibody capable of binding to an antibody directed to the antigen and to a receptor of the antigen, (e) separately culturing a hybridoma cell so identified in an appropriate medium, and (f) separately recovering under suitable conditions the monoclonal anti-idiotypic antibody produced by the hybridoma cell.

Suitable animals for use with this auto-anti-idiotypic method include vertebrates such as mice, rats, rabbits, guinea pigs, pigs, goats and cows. Additionally, human and other vertebrate lymphoid cells may suitably be used in embodiments using in vitro immunization.

This method provides a more direct route than any previously available for obtaining a monoclonal antibody that binds to, or more preferably mimics the biological activity of a receptor or ligand, e.g. as an agonist or antagonist. The antigen comprises a naturally occurring or synthetic molecule capable of binding to a receptor Suitable receptors include an adenosine receptor; acetylcholine receptor (AChR); steroid receptor, e.g. estrogen, androgen or glucocorticoid receptor; thyroid stimulating hormone (TSH, thyrotropin) receptor; insulin, or other protein receptor; β-adrenergic receptor; dopamine receptor or one of the chemotactic receptors of the neutrophil. The invention is further applicable to receptors for other pharmacologically active low molecular weight molecules, for regulatory macromolecules such as lymphokines, and for infectious agents such as viruses, and to other receptors as defined above. The monoclonal anti-idiotypic antibody so produced is capable of binding to the receptor and may additionally act as an agonist or antagonist with respect to the receptor. In this and other embodiments (including embodiments wherein the antigen is not a ligand for a receptor) the antigen may be conjugated to a protein such as a serum albumin, e.g. bovine or rabbit serum albumin, or a protein such as keyhole limpet hemocyanin or thyroglobulin, and is preferably injected into the animal with a suitable adjuvant, e.g. complete Freund's adjuvant, or is used for in vitro immunization of lymphoid cells grown in culture (26).

In a specific embodiment of the invention the animal is injected intraperitoneally with a bovine serum albumin (BSA) conjugate of 4-(2'-succinoyloxyethyloxy)-trans-3,3'-bis(α-trimethylammonium)azotoluene (1), depicted below.

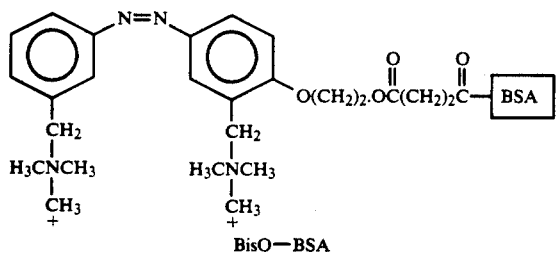

BisO—BSA

The synthetic compound containing the antigenic determinants of interest, trans-3,3'-bis(α-trimethylammonium)azotoluene (BisQ), depicted below, is a powerful agonist of AChR (1).

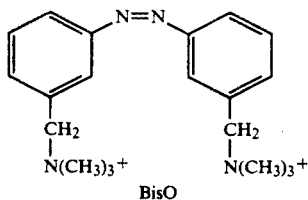

BisO

Thus, when a mouse was immunized with a bovine serum albumin conjugate of BisQ (BisQ-BSA) as depicted above, it was possible to expand populations of spleen cells that secrete antibodies which bind anti-BisQ and AChR, in addition to populations specific for BisQ. Fusion of the spleen cells with an appropriate myeloma cell line, essentially by the protocol of Kohler and Milstein (17) as modified by Sharon et al. (18), yielded monoclonal anti-AChR antibodies. This experimental result, as well as work by other researchers (2,16) lends support to Jerne's theory of a functioning idiotypic network (15).

Similarly, monoclonal anti-adenosine receptor antibodies were obtained when the animal was injected intraperitoneally with a bovine or rabbit serum albumin conjugate of $N^6$-carboxypentamethylene adenosine (CPA) depicted below.

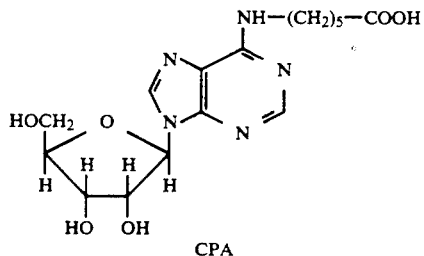

CPA

In this embodiment the compound containing the antigenic determinants of interest is the naturally-occurring molecule, adenosine.

In another example monoclonal antibodies to glucocorticoid receptors were obtained by immunizing an animal with a protein conjugate of an appropriate compound. As in the BisQ and adenosine examples described above, the compound containing the antigenic determinants of interest, in this case the glucocorticoid receptor triamcinolone (9-fluoro-11β, α16, 17, 21-tetrahydroxypregna-1,4-diene-3, 20-dione), is conjugated to a suitable protein with a linker moiety, here ketohexanoic acid. The structure of triamcinolone and the linker moiety is depicted in FIG. 1. Additionally, the complete synthetic route used to prepare the triamcinolone protein conjugate is depicted schematically in FIG. 1.

An effective antibody-raising amount of antigen or antigen-protein conjugate may be provided by about 0.1 ml of a solution containing about 1 mg/ml of the antigen or conjugate, preferably with an adjuvant such as complete Freund's adjuvant. Preferably, about two to about four weeks, e.g. about 3 weeks after the injection, the animal is injected again with a booster injection of a solution of the antigen. After another period of about two to about four weeks the booster injection may be repeated. At a suitable time after the injection, e.g. at least about three days after the last booster injection, lymphoid cells are collected from the animal, for example by sacrificing the animal and collecting the spleen cells.

Alternatively, lymphoid cells may be contacted with the antigen more directly by culturing the lymphoid cells in vitro in the presence of the antigen (26). The lymphoid cells may be collected, again, at least about three days after the immunizing contact with the antigen. A series of hybridoma cells is then prepared essentially by the protocol of Kohler and Milstein (17) as modified by Sharon et al. (18), as indicated above.

Supernatants from the hybridoma culture medium may then be obtained by a replica transfer technique (19) and screened for activity by immunoassay against the antigen or conjugate, an immobilized antibody to the antigen or conjugate (idiotypic) and in embodiments where the antigen is a ligand to a receptor, against the appropriate receptor. The immunoassay also requires a labeled antibody capable both of binding to the antiidiotypic monoclonal antibody under appropriate conditions and of being detected. Preferably the immunoassay is enzyme-linked (1) using, e.g., peroxidase-labeled goat anti-mouse immunoglobulin as the labeled antibody in embodiments for producing the monoclonal antibodies from mouse spleen cells.

In the case of BisQ about 7.4% of the hybridoma cells were positive for purified rabbit anti-BisQ, of which about one-third were also positive for AChR (Torpedo).

Similar results were obtained with CPA, after screening with a rabbit anti-CPA antibody and with a preparation of adenosine receptor obtained from rat brain by the procedure of Gavish et al. (20). Similar results were also obtained with triamcinolone, after screening the hybridoma culture medium using a double antibody sandwich ELISA employing affinity purified rabbit antisteroid Fab fragments and goat anti-mouse antibodies labeled with horseradish peroxidase. Thus, not only is the idiotypic network functioning during a normal immunization process (21), it is functioning very actively, as early as five days after a first booster injection.

After they were identified, positive wells were then subcloned by the procedure of limiting dilution. In the BisQ-BSA embodiment several of the clones that produced antibody reactive with both anti-BisQ and Torpedo receptor were examined. FIG. 2 shows titrations by enzyme immunoassay of an $(NH_4)_2SO_4$ precipitate of a supernatant from one clone, F8-D5. The antibody produced by this clone was able to bind AChR of Torpedo as well as specifically purified rabbit anti-BisQ. This property was retained by clones obtained after two subsequent subclonings by limiting dilution. No attempt can be made to relate the respective binding affinities because of the characteristics of enzyme immunoassay procedures, in general. For example, there is no way to ensure that the same number of determinant sites of receptor and of anti-BisQ adhere to the plastic wells.

Figure 3:
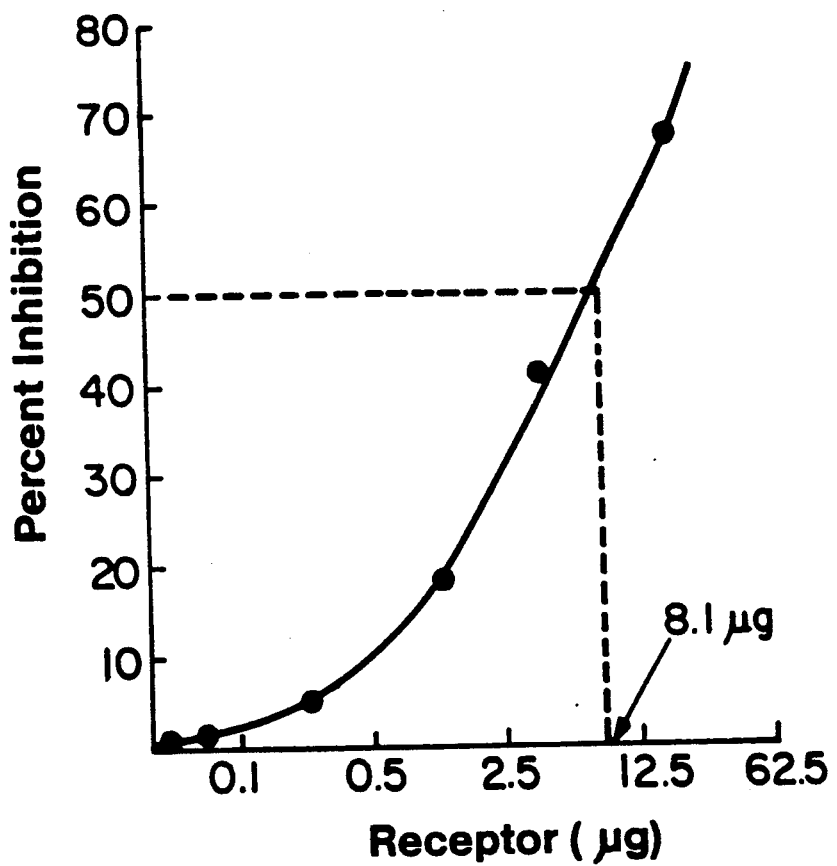
FIG. 3. Illustrates inhibition of binding of F8-D5 monoclonal anti-idiotypic antibody to anti-BisQ by Torpedo AchR.

To confirm that the same monoclonal antibody bound receptor and anti-BisQ, reciprocal inhibition experiments were carried out. FIG. 3 shows the results of an experiment in which the binding to anti-BisQ of an $(NH_4)_2SO_4$-precipitated supernatant of F8-D5 was inhibited by Torpedo receptor. At the highest concentration of receptor used, 67% inhibition was observed; 50% inhibition occurred with about 8 micrograms of inhibitor in the conditions described in Example 4, below. In experiments in which the amount of antibody was decreased five-fold to 2 micrograms per well, 50% inhibition occurred in the presence of 0.9 micrograms of Torpedo receptor. In a similarly designed series of experiments, 50% inhibition of the binding of F8-D5 monoclonal antibody to Torpedo receptor was accomplished with 3 micrograms of purified rabbit anti-BisQ.

The binding of F8-D5 to Tropedo receptor could be inhibited by BisQ, 50% inhibition occurring at a concentration of $4 \times 10^{-5}$M. A similar concentration of BisQ caused 50% inhibition of the binding of F8-D5 to rabbit anti-BisQ. These results reinforce the conclusion that the specificity of F8-D5 is for determinants intimately associated with the combining sites of both the Torpedo receptor and rabbit anti-BisQ. With respect to the latter, this is consistent with a specificity for an idiotypic determinant. It is important to note that BisQ is a small molecule (molecular weight 486) and not likely to block reaction with non-idiotypic determinants near the combining site as a result of steric interference.

Since F8-D5 arose in mice by immunizing with BisQ-BSA, rather than with rabbit anti-BisQ, it can be concluded that an auto-anti-idiotypic immune response occurred. Thus, it seems that idiotypic determinants are shared by rabbit and mouse anti-BisQ.

Figure 4:
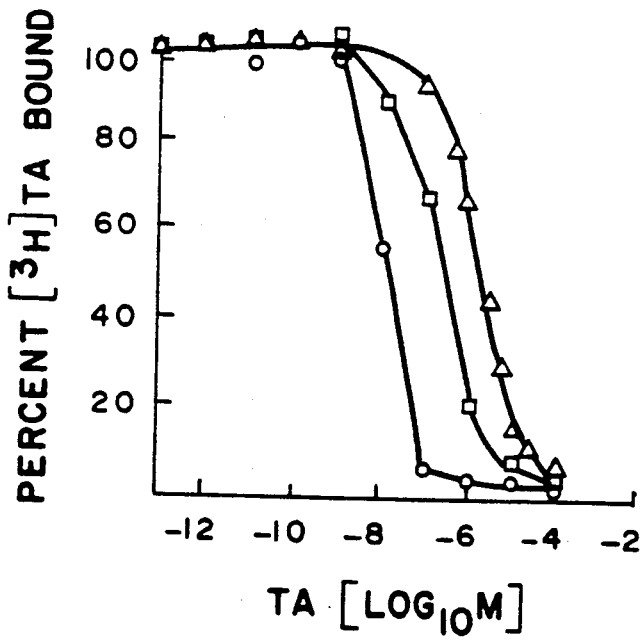
FIG. 4. Competitive inhibition of binding of [$^3$H]TA to the rat liver cytosol by increasing levels of unlabeled triamcinolone acetonide (◯), steroid derivative 17-[C4-carboxy-1-methylbutylidine)bis(oxy)]-9-fluoro11$\beta$-21-dihydroxypregna-1,4-diene (☐), and by the steroid-BSA conjugate (△). Incubate in a total volume of 500 microliters, for 2 hrs at 4° C., 20 mM HEPES buffer containing 50 mM NaCl, 1 mM EDTA, 10% glycerol 0.1 mM DTT pH 7.6, 10 nM [$^3$H]TA and 200 microliters rat liver cytosol. Add 250 microliters 5% charcoal/dextran suspension and after 10 min centrifuge and determine the radioactivity in 200 $\lambda$ aliquot.

The TA-BSA conjugate was found to compete with tritiated triamcinolone [$^3$H]TA for the glucocorticoid receptor Its apparent Kd at 10 nM [$^3$H]TA for the glucocorticoid receptor was found to be $2.5 \times 10^{-6}$M. This is 100-fold greater than that of the ligand, triamcinolone acetonide which was found to be $1.5 \times 10^{-8}$M under the same assay conditions (FIG. 4).

The triamcinolone-BSA conjugate was also found to be immunogenic and to induce polyclonal antibodies specific for triamcinolone. Significant titers could be detected in rabbit serum immediately after the second booster injection. These were detected by preciptin tube assay by incubating rabbit serum with various concentrations ranging from 0.1-1.0 mg/ml of either triamcinolone-RSA or RSA. Precipitation was only obtained in the presence of triamcinolone-RSA and not with RSA. When pre-immune serum was used as a control, no precipitation was obtained. Portions of the anti-serum were then purified by affinity chromatography on an AH-Sepharose 4B-triamcinolone column. 40 ml of serum yielded 15-20 mg anti-steroid, that could also precipitate the triamcinolone-RSA complex by the preciptin tube assay as well as by Ouchterlony.

For the antisteroid experiments, 100 microliters of unprocessed rabbit serum 540 (dil 1:1000 in PBS) or affinity purified anti-steroid pH 2.5 (1.3 micrograms) or FAB fragments (0.18 micrograms) was incubated with $10^{-8}$M [$^3$H]TA and increasing concentrations of steroid in a total volume of 200 microliters. After incubating for 1½ hrs at room temperature add 1 ml cold 5% charcoal/dextran (dil 1:40 with 0.1% gelatin in PBS). Let stand at 4° C. for 10 mins. Centrifuge down charcoal, decant supernatant into scintillation vials, add 10 ml hydrofluor and count.

The results tabulated in table I below represents the amount of unlabeled steroid that can displace 50% binding of $1 \times 10^{-8}$M [$^3$H]TA. Binding in the absence of competing steroid was taken as 100%.

TABLE I

| Steroid | Glucocorticoid receptor [M] | Rabbit Serum 540 Unprocessed [M] | Rabbit Serum 540 Affinity purified [M] | Rabbit serum 541 Fab fragments [M] |
|---|---|---|---|---|
| Triamcinolone | $5 \times 10^{-9}$ | $3.2 \times 10^{-9}$ | $1.5 \times 10^{-8}$ | $1.5 \times 10^{-8}$ |
| Dexamethasone | $7.9 \times 10^{-9}$ | $1.2 \times 10^{-7}$ | $6.2 \times 10^{-7}$ | $6.3 \times 10^{-7}$ |
| Corticosterone | $3.1 \times 10^{-8}$ | $6.3 \times 10^{-6}$ | $1.0 \times 10^{-4}$ | $1.0 \times 10^{-4}$ |
| Hydrocortisone | $1.2 \times 10^{-7}$ | $5.0 \times 10^{-6}$ | $1.0 \times 10^{-4}$ | $1.0 \times 10^{-4}$ |
| Progesterone | $2.5 \times 10^{-6}$ | $1.0 \times 10^{-4}$ | $1.0 \times 10^{-4}$ | $1.0 \times 10^{-4}$ |
| Testosterone | no inhibition | not inhibited | not inhibited | not inhibited |

Table I: Competitive inhibition of binding of [$^3$H] triamcinolone to the glucocorticoid receptor, unprocessed rabbit serum 540, affinity purified anti-steroid and anti-steroid Fab fragments. Assays with the glucocorticoid receptor included 100 ml of rat liver cytosol. $10^{-8}$M [$^3$H]TA and increasing concentrations of steroid in a total volume of 200 ml. After incubating for 2 hrs at 4° C., 100 5% charcoal/dextran was added. Let stand for 5 mins at 4° C. Make up to 1 ml with PBS and after 5 mins centrifuge down charcoal. Decant supernatant into scintillation vials. Add 10 ml hydrofluor and count.

Figure 5:
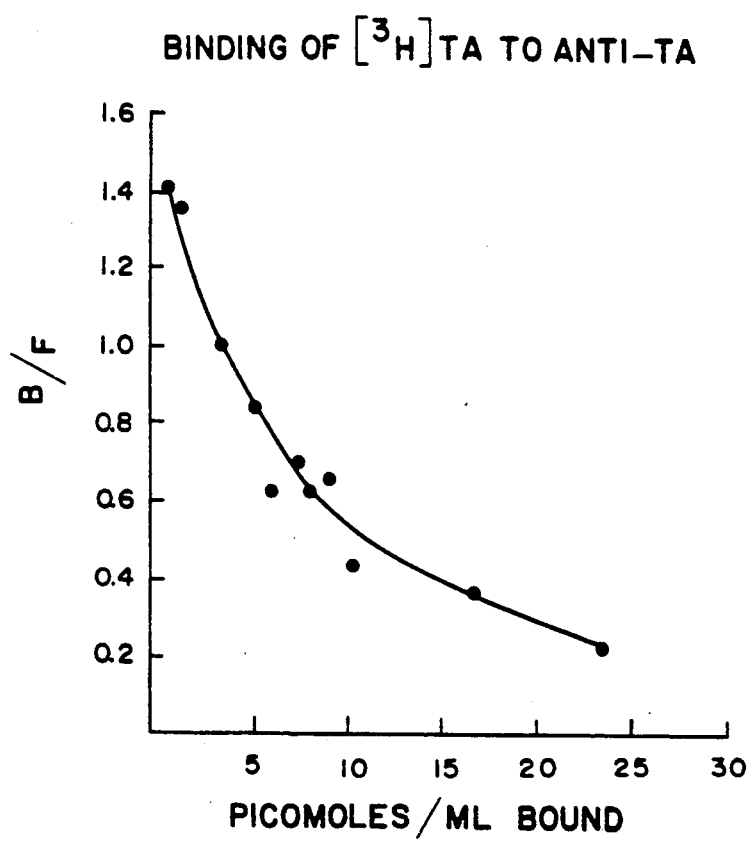
FIG. 5. Scatchard plot of the binding of [$^3$H]triamcinolone acetonide to Fab fragments of affinity purified anti-steroid antibodies. Fab fragments (0.227 micrograms) were incubated with increasing concentrations of [$^3$H]triamcinolone acetonide (0.4-62.5 nM) in the presence of 0.01M phosphate buffered saline pH 7.4 containing 0.1% gelatin in a total volume of 200 microliters. Total and non-specific binding (50 micromolar triamcinolone acetonide) were determined for each of the [$^3$H]triamcinolone acetonide levels and all points were in duplicate. After incubating 1 hr at room temperature, add 1 ml cold 5% charcoal/dextran (diluted 1:40 in 0.01M PBS containing 0.1% gelatin) and let stand on ice for 10 min. Centrifuge down the charcoal/dextran, decant the supernatant into scintillation vials and determine the radioactivity.

Both the affinity purified polyclonal idiotypic, i.e., anti-steroid, antibodies as well as their Fab fragments, were found to bind [$^3$H]TA. The Kd for Fab fragments of the anti-steroid, as determined from Scatchard plots (FIG. 5), ranged from $9.3 \times 10^{-9}$M to $4.3 \times 10^{-8}$M. The curved plot clearly indicates the heterogeneous nature of the anti-steroid idiotype. On the other hand, a linear Scatchard plot was obtained with [$^3$H]-dexamethasone and the Kd for the anti-steroid FAB fragments determined to be $1.5 \times 10^{-7}$M.

Figure 6:
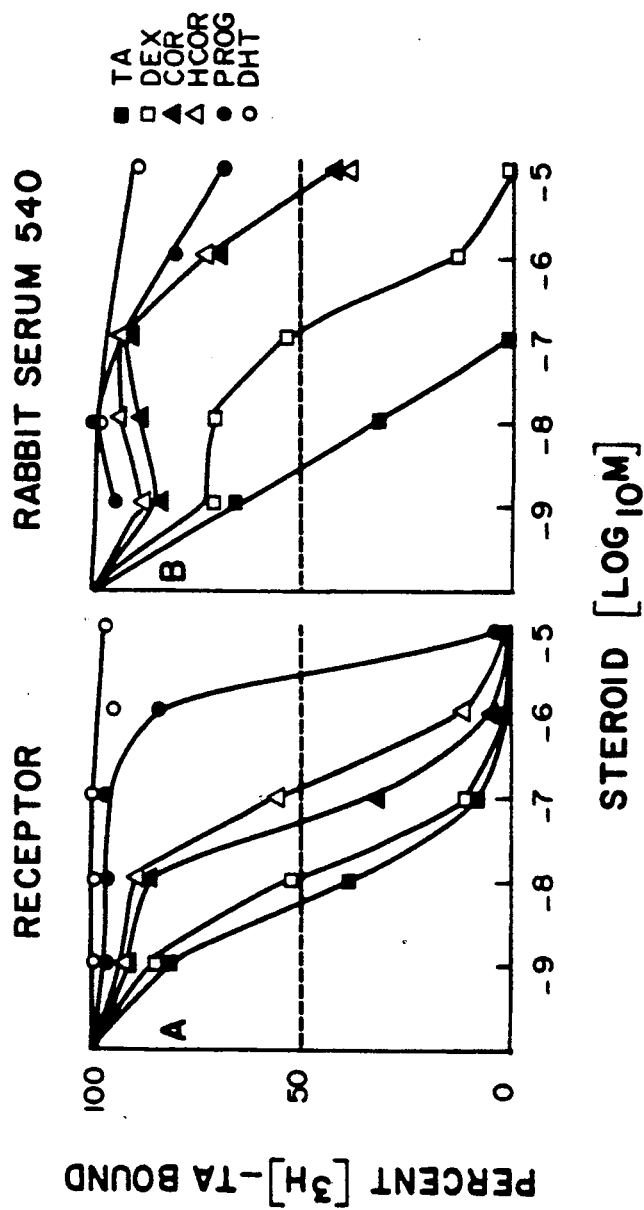
FIG. 6. Competitive inhibition of binding of [$^3$H]triamcinolone to the glucocorticoid receptor and to anti-steroid (unprocessed rabbit serum 540). See legend to Table I for the experimental procedure. The inhibitors used were triamcinolone acetonide (■), dexamethason (☐), corticosterone (▲), hydrocortisone (△), progesterone (●), and dihydrotestosterone (◯).

The ligand binding properties of these polyclonal antibodies closely resembled those of the glucocorticoid receptor Competitive binding studies with [$^3$H]TA as the tracer showed that their pattern of steroid inhibition was similar for the glucocorticoid receptor and the antibody. Triamcinolone was the most potent inhibitor, followed in descending order of potency as an inhibitor by dexamethasone, corticosterone, hydrocortisone and progesterone. Dihydrotestosterone had no effect on the binding of [$^3$H]TA to either the glucocorticoid receptor or to the rabbit anti-TA antibody (FIG. 6, Table I). The apparent Kd of the anti-steroid in unprocessed rabbit serum for triamcinolone acetonide ($3.2 \times 10^{-9}$M) was similar to that of the glucocorticoid receptor ($5 \times 10^{-9}$M) whereas those of the other steroids were about one order of magnitude lower. Although the apparent dissociation constants of the various steroids for the affinity purified antibodies were similar to those of their respective FAB fragments, they were considerably lower than those of the unprocessed serum, indicating that some of the high affinity antibodies were lost during the affinity purification procedure.

As the steroid binding properties of the glucocorticoid receptor and those of the Fab fragments of the affinity purified anti-steroid antibodies were similar, the latter were used to screen by ELISA for anti-idiotypic antibody production in mice.

Isolation of anti-idiotypic antibodies to Fab fragments and the subsets that reacted with the clucocorticoid receptor Autoantiidiotypic antibodies to the anti-steroid antibodies were raised by immunizing a mouse with a triamcinolone-thyroglobul in conjugate. After the mouse spleen cells were fused with the non-secreting myeloma cell line P3x63-AG8.653, 17 cell lines were found to produce antibodies that bound to the Fab fragments in ELISA assay. However, only 5 of these remained positive after the cell lines were expanded.

Antibodies cross reacting with the glucocorticoid receptor were selected from among the anti-idiotypes by their ability to deplete glucocorticoid receptor from rat liver cytosol. The anti-idiotypes were first immobilized on CNBr-Sepharose anti-mouse beads and incubated with rat liver cytosol. After 2 hrs, the beads were centrifuged down and the cytosol [$^3$H]TA. To account for non-specific binding of the glucocorticoid receptor to the beads controls were included. In these either no anti-idiotype or an anti-idiotype namely 5B5 that did not interact with the anti-steroid by ELISA wa immobilized on the beads.

Of all the anti-idiotypic antibodies tested, only 8G11, an IgM, was found to bind to the glucocorticoid receptor. As can be seen from Table II, rat liver cytosol treated with 8G11, immobilized on CNBr-Sepharose anti-mouse beads would bind 15% less [$^3$H]TA, whereas 5B5 bind only 3% less 3H]TA when compared with cytowould sol incubated with CNBr-Sepharose anti-mouse beads containing no anti-idiotype. From Table II, it can also be seen that this depletion was dependent on the amount of rat liver cytosol used in the assay. The amount of gluco-corticoid receptor depleted by 8G11-C6 was increased from 15% to 40% by diluting the cytosol containing the glucocorticoid receptor.

TABLE II

| | Cytosol Dil. 2 × | | Cytosol Dil. 4 × | |
|---|---|---|---|---|
| | cpm | % depleted | cpm | % depleted |
| Receptor + BM + 10% FES | 4723 | — | 1682 | — |
| Receptor + 5B5 | 4851 | 3 | 1884 | — |
| Receptor + 8G11 | 3998 | 15 | 1013 | 40 |

Table II: Depletion of glucocorticoid receptor from rat liver cytosol. For the experimental procedure used see methods.

8G11 was subcloned and the monoclones 8G11-G5 and 8G11C-6 were derived from this line. These were partially purified by precipitating in 50% $(NH_4)_2SO_4$. From Table II, it can be seen that CNBr-Sepharose anti-mouse beads that had no antibody attached to them and treated with BM containing 1% FCS depleted 5% of [$^3$H]TA from rat liver cytosol when compared to anti-mouse beads treated with PBS. Antimouse beads with the immobilized control cell line 5B5 or 5B5-B6 also depleted 9% and 4%, respectively, of [$^3$H]TA from rat liver cytosol when compared to the control antimouse beads that were treated with PBS. As more [$^3$H]TA receptor was removed from rat liver cytosol by 8G11-C6 than by 8G11-C5 and as the 8G11-C6 cell line resembled the parent cell line 8G11 more closely than 8G11-C5, it was used in all the remaining characterization studies. The hybridoma cell line secreting 8G11-C6 has been deposited with the American Type Culture Collection, Rockville, Md. under accession number ATCC HB 8708.

Table III shows that prelabeling the receptor by preincubating rat liver cytosol with low levels of [$^3$H]TA (2.5 nM) or high levels [$^3$H]TA (13nM-50nM) for 2 hrs at 4° C. and then adding it to CNBr-Sepharose 4B antimouse 8G11-C6 does not inhibit the binding of receptor to the beads. This was again verified by the finding that less cpm (30-65%) were obtained when 8G11-C6 was bound to the beads when compared to 5B5-B6. The epitope recognized by the anti-idiotypic 8G11-C6 therefore might lie near but not in the ligand binding site of the glucocorticoid receptor.

TABLE III

|  | 2 × 5 nM [$^3$H]TA | | 13.0 nM [$^3$H]TA | | 50.0 nM [$^3$H]TA | |
| --- | --- | --- | --- | --- | --- | --- |
|  | cpm | % depleted | cpm | % depleted | cpm | % depleted |
| Receptor + PBS | 1124 | | | | | |
| Receptor + 5B5 | 1232 | 0 | | | | |
| Receptor + 5B5-B6 | 1354 | 0 | 1345 | 0 | 1347 | 0 |
| Receptor + 8G11 | 503 | 61 | | | | |
| Receptor + 8G11-C6 | 449 | 65 | 934 | 30 | 646 | 52 |

Table III: The effect of prelabeling glucocorticoid receptor with [$^3$H]TA on its removal from rat liver cytosol. The procedure described in the methods section was used, the only difference being that the [$^3$H]TA levels indicated in the Table were used. Also, at high [$^3$H]TA levels (5.0 nM [$^3$H]TA) an additional step was included whereby the supernatant (275 microliters) obtained after the charcoal/dextran step was passed over a dry sephadex G50 column (5 cc capacity) to remove any free [$^3$H]TA.

Figure 7:
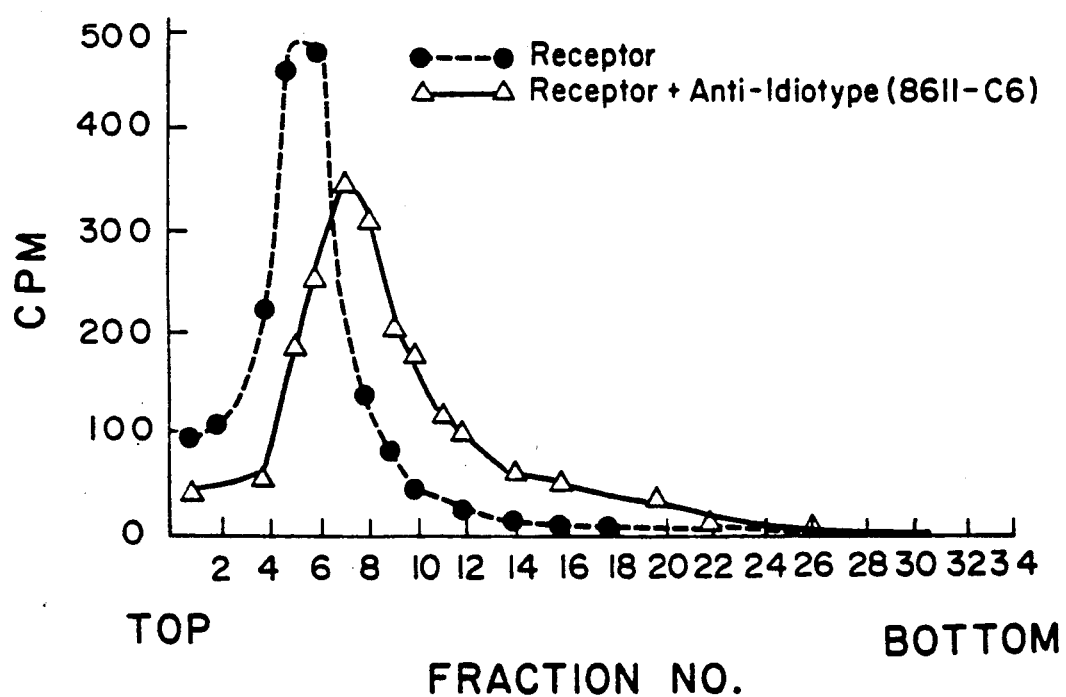
FIG. 7. Sucrose density gradient analysis. Rat liver cytosol (●—●), rat liver cytosol and 8G11-C6 (△—△).

More direct evidence of binding of 8G11-C6 to [$^3$H]TA glucocorticoid receptor was obtained from sucrose density studies. As can be seen in FIG. 7 incubation of [$^3$H]TA receptor with 8G11-C6 causes a shift and spread of the elution profile of the glucocorticoid receptor to the right, indicating a protein:protein interaction. However, when assaying by ELISA using goat anti-mouse IgM to detect the position of 8G11-C6 in the various fractions of the sucrose gradient, IgM was found at the bottom of the tube. From this, it would be expected the [$^3$H]TA receptor:antibody complex should move to the bottom of the tube if no dissociation of the complex occurs during centrifugation.

Characterization of 8G11-C6 by ELISA

1. Specificity of binding of 8G11-C6 to Fab fragments

Figure 8:
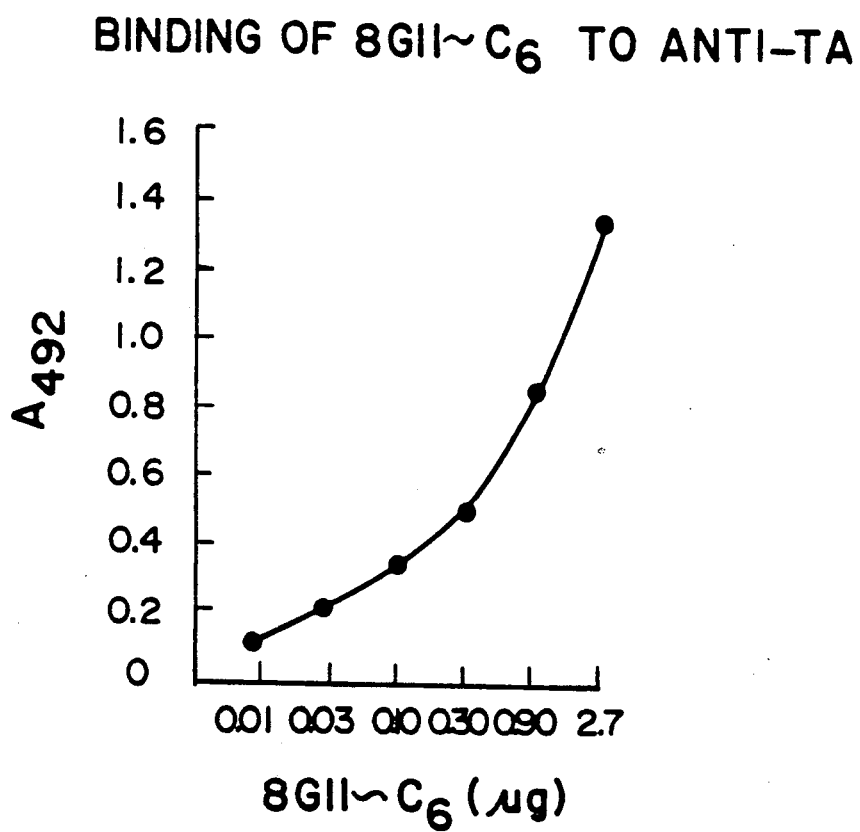
FIG. 8. Binding of 8G11-C6 to anti-steroid Fab fragments. See methods for the experimental procedure. 8G11-C6 was partially purified by precipitating with 50% (NH$_4$)SO$_4$.
Figure 9:
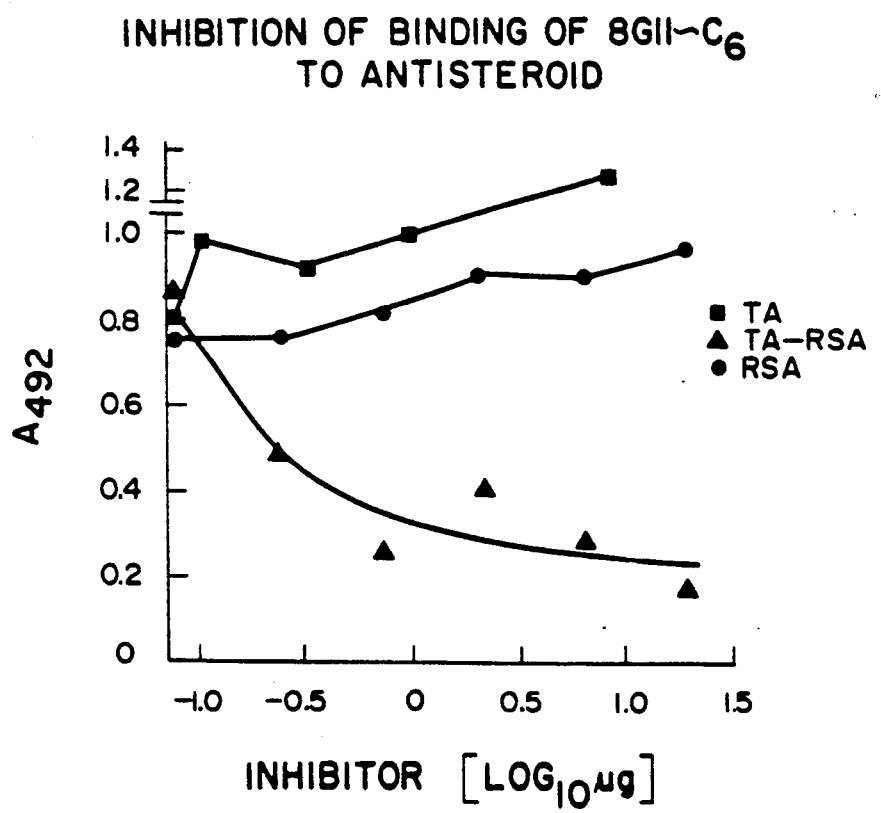
FIG. 9 and 10. The effect of various steroids, steroid conjugates and RSA on the binding of 8G11- C6 to anti-steroid-Fab fragments. The method used was similar to that described in the experimental procedure; the only difference being that 155 microliters of inhibitor that was diluted serially 2-fold with PBS was added to each well and pre-incubated at room temperature for 10–20 min. Controls with no inhibitor were included. Add 25 $\lambda$ of 50% (;NH$_4$)$_2$SO$_4$ precipitated 8G11-C6 (1.045 micrograms) mix and incubated for 2 hrs at 37° C. Blanks with only PBS were included as well. The inhibitors used in FIG. 9 were triamcinolone acetonide (■), triamcinolone-RSA (▲) and rabbit serum albumin (●). The inhibitors used in FIG. 10 were estradiol 17$\beta$-RSA (●), testosterone-RSA (◯), triamcinolone-RSA (■), deoxycorticosterone-RSA (▲) and cortisone-RSA (△).
Figure 10:
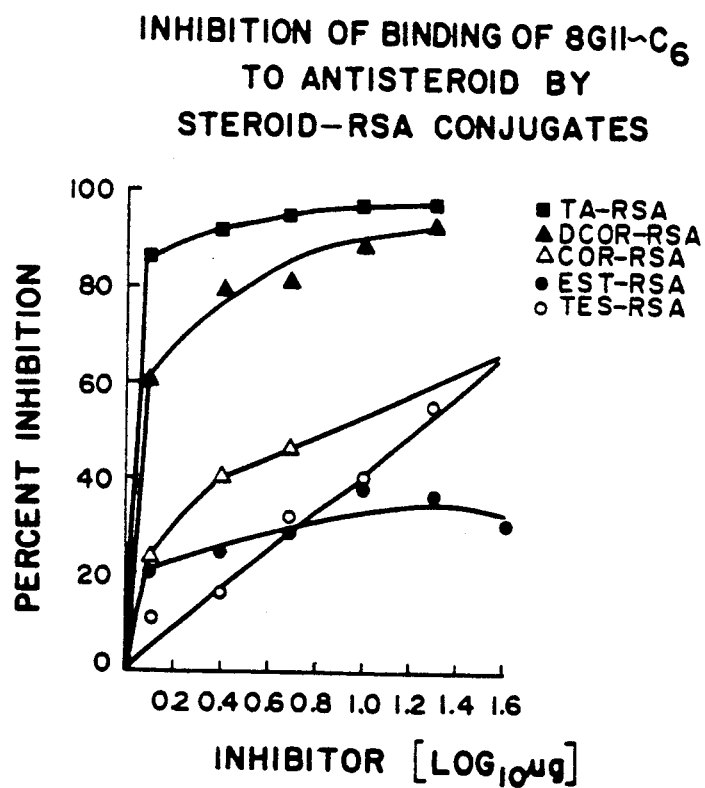

The binding of 8G11-C6 to Fab fragments was found to be concentration dependent (FIG. 8). Although it was found that the ligand, triamcinolone acetonide, or rabbit serum albumin on their own did not affect the binding of 8G11-C6 to Fab, the steroid conjugate i.e. triamcinolone-RSA did inhibit the binding of 8G11-C6 to Fab (FIG. 9). In addition, to triamcinolone-RSA, other steroid-RSA conjugates such as deoxycorticosterone-RSA and cortisone-RSA were also found to inhibit the binding of 8G11-C6 to the antisteroid-Fab fragments. On the other hand, testosterone-RSA and estradiol-17$\beta$-RSA were found to have only a slight inhibitory effect (FIG. 10). The pattern of inhibition of binding of 8G11-C6 to antisteroid-Fab by the steroid-RSA conjugates resembled that obtained with the competitive binding studies of various steroids with [$^3$H]TA for receptor and anti-steroid antibodies. Neither triamcinolone, nor other steroids such as testosterone and oestradiol-17B had any effect on the binding of 8G11-C6 to the antisteroid-Fab fragments. In fact, they appear to produce a slight activation of binding.

Figure 11:
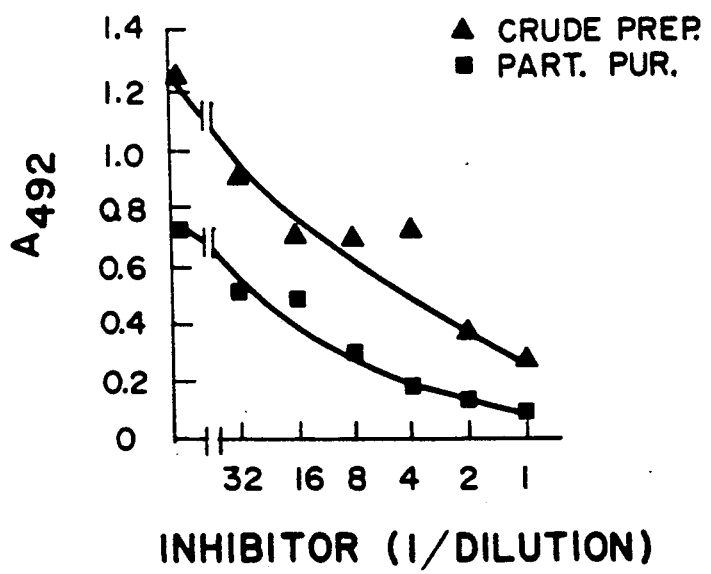
FIG. 11. Inhibition of binding of 8G11-C6 to anti-steroid Fab fragments with rat liver cytosol (▲) or partially purified glucocorticoid receptor (■). The method used was similar to that described in the experimental procedure. The only difference being that, to 200 $\lambda$ of rat liver cytosol or partially purified glucocorticoid receptor preparations, that were diluted 2-fold serially in PBS, 1.045 micrograms of 50% (NH$_4$)$_2$SO$_4$ precipitated 8G11-C6 was added and pre-incubated at room temperature for 15 mins. 200$\lambda$ of the incubation mixture was then added to microtiter wells previously coated with 10 ng anti-steroid Fab fragments and incubated for 2 hrs at 37° C.

The binding of 8G11-C6 to Fab was also inhibited by rat liver cytosol which contains glucocorticoid receptor (FIG. 11). As it could be argued that any other protein or substance in cytosol could cause this inhipition, the glucocorticoid receptor was partially purified from rat liver cytosol. As can be seen from FIG. 11, preparations of partially purified glucocorticoid receptor also inhibited the binding of 8G11-C6 to Fab, having enhanced activity at comparable dilutions.

Figure 12:
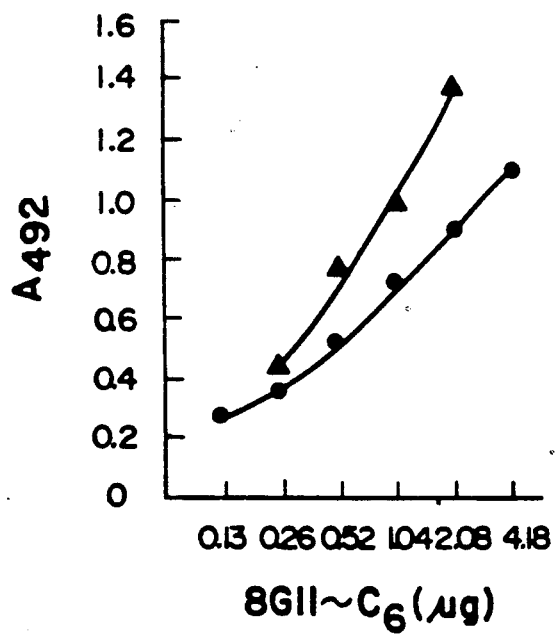
FIG. 12. Binding of 8G11-C6 to partially purified glucocorticoid receptor. 200 microliters containing either 1.08 micrograms (▲) or 0.54 micrograms (●) of a partially purified receptor preparation in 0.1 M NaHCO$_3$ were added to the wells of the polystyrene plastic and incubated overnight at 4° C. The wells were washed 2× with PBS-Tween and various amounts of a 2-fold serialy diluted 50% (NH$_4$)$_2$SO$_4$ precipitated preparation of 8G11 C6 added. See methods section for the methodology employed.

2. Specificity of binding of 8G11-C6 to partially purified glucocorticoid receptor As can be seen from FIG. 12 the binding of 8G11-C6 to plates coated with partially purified glucocorticoid receptor was concentration dependent.

Figure 13:
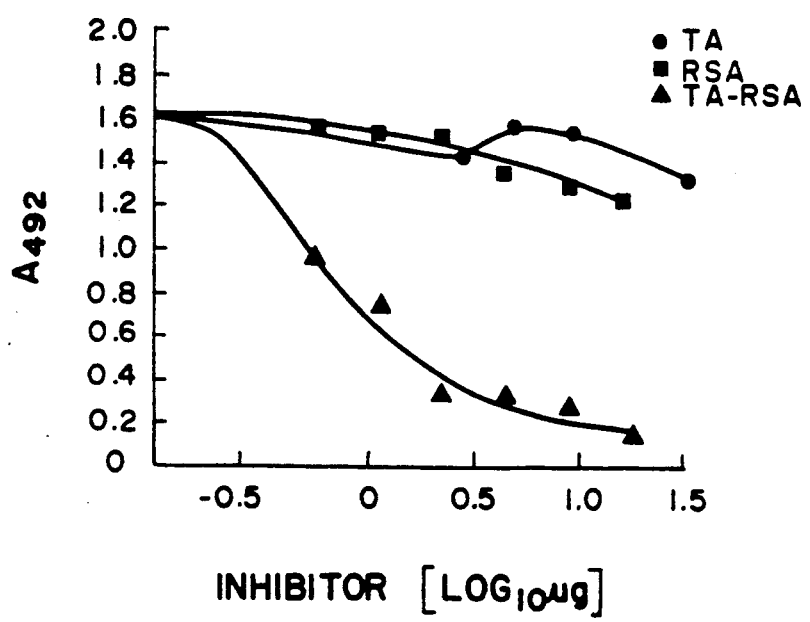
FIG. 13. Inhibition of binding of 8G11-C6 to partially purified 91ucocorticoid receptor. 200 microliters containing 0.54 micrograms protein of a partially purified receptor preparation in 0.1 M NaHCO$_3$ pH 9.3 was added to the wells of polystyrene plates. These were incubated for 2 hrs at 37° C. Washed 2× with PBS containing 0.02% Tween. Add 175 1 of inhibitor serially diluted 2-fold and pre-incubate for 20 min at room temperature before adding 0.836 micrograms of 50% (NH$_4$)$_2$SO$_4$ ppt of 8G11-C6, mixing and incubating for 2 hrs at 37° C. See methods for the methodology employed. The inhibitors used were triamcinolone acetonide (●), rabbit serum albumin (■) and triamcinolone-RSA (▲).

The binding of 8G11-C6 to partially purified receptor was inhibited by triamcinolone-RSA but not by triamcinolone or rabbit serum albumin (FIG. 13). Deoxycorticosterone-RSA also inhibited the binding of 8G11-C6 to partially purified rat liver glucocorticoid receptor. Testosterone had only a slight inhibitory effect whereas estradiol-17$\beta$ had no effect on this binding. These findings indicate that 8G11-C6 binds to a protein in the partially purified preparations that interacts with the steroid conjugate.

To summarize the triamcinolone embodiment briefly, data obtained in the various studies of the 8G11-C6 monoclonal antibody show that it is specific for rat liver glucocorticoid receptor. The 8G11-C6 antibody was obtained by an auto-anti-idiotypic route, as were the other embodiments of this invention.

The strategy employed was to use the hapten, triamcinolone, of the glucocorticoid receptor to raise polyclonal antibodies in rabbits and monoclonal antibodies in mice. In the rabbits only polyclonal idiotypic anti-steroid antibodies were isolated by affinity chromatography. These were used to screen by ELISA for anti-idiotypic antibody formation in mice using a goat anti-mouse peroxidase label. However, as this is a polyclonal system only, some and not all of the idiotypic antibody subsets present will mimic the glucocorticoid receptor. Furthermore, the receptor-like idiotypes in this population would not necessarily represent the majority. This would require more specific techniques than those used in the present study to elute the anti-steroid from the affinity column. Attempts to elute anti-steroid with the ligand triamcinolone proved fruitless. For this reason, specific anti-idiotypes that would bind to the glucocorticoid receptor were selected for, by immobilizing anti-idiotypic antibodies to CNBr-Sepharose antimouse beads and testing their ability to remove high affinity [$^3$H]TA binding from rat liver cytosol. This strategy resembles that used to isolate anti-idiotypic antibodies to the acetylcholine receptor (36). The major difference between the two being that purified acetylcholine receptor was used to screen for anti-idiotypic acetycholine activity in the former study whereas in the present study anti-idiotypic glucocorticoid receptor activity was determined with crude rat liver cytosol preparations by a depletion assay and verified with characterization studies. This demonstrated that purified receptor preparations were not necessary either for immunizing or screening. Other anti-idiotypic antibodies that are cross reactive with insulin receptor (37), chemotactic receptors of the neutrophil (40), B-adernergic receptor (38,39), Reovirus receptor (41), dopamine receptor (42), and TSH receptor (43) have also been raised by using ligand and/or idiotypic antibodies as antigens.

In order to induce antibodies, with ligand-like properties the first requirement was to make a hapten that could interact with the glucocorticoid receptor. For this reason, triamcinolone was derivatized to triamcinoloneδ-ketohexanoic hydroxysuccinimide ester at the 16 and 17 position of the D ring of the steroid, as this modification would affect its binding activity to the receptor the least. The triamcinolone protein conjugates that were synthesized from the steroid ester interacted with the glucocorticoid receptor and elicited both idiotypic and anti-idiotypic antibodies. The polyclonal idiotypes raised by the triamcinolone-BSA conjugate in rabbits had high affinities for triamcinolone acetonide and steroid binding specificities that resembled those of the glucocorticoid receptor. The anti-idiotypes, and in particular 8G11-C6, obtained from mouse hybridomas, that were raised by immunizing with triamcinolone-thyroglobulin, bound the idiotypes specifically. The binding of 8G11-C6 to the anti-steroid was inhibited by triamcinolone-RSA conjugates and amino acids and peptides containing triamcinolone, indicating that this interaction occurred at the combining site of the idiotype. It was also shown that the 8G11-C6 cross-reacted with the 9lucocorticoid receptor in crude rat liver cytosol preparations. This was confirmed by the findings that partially purified glucocorticoid receptor preparations also inhibited the antisteroid idiotype from reacting with the anti-idiotypic 8G11-C6. Furthermore, the cross reaction of 8G11-C6 with partially purified glucocorticoid receptor preparation was inhibited by triamcinolone-RSA conjugates. Also, the patterns of inhibition of binding of 8G11-C6 to the antisteroid and of 8G11-C6 to the glucocorticoid receptor by different steroid-RSA conjugates were similar. These ELISA results established the interrelationship of hapten-idiotype, anti-idiotype and glucocorticoid receptor.

The anti-idiotype 8G11-C6 was initially raised to idiotypic antibodies that were specific for triamcinolone. However, the results show the binding of 8G11-C6 to the antisteroid is inhibited by steroid-RSA conjugates rather than by triamcinolone acetonide. As the ligand is a low M.W., organic molecule it will only occupy a small portion of the total combining surface area of the antisteroid. Hence 8G11-C6 will be able to crossreact with the antisteroid even though triamcinolone is present. On the other hand, in the case of the steroid-RSA conjugate almost the total area will be occupied and the binding of 8G11-C6 to the antisteroid will be inhibited. This is supported indirectly by the finding that the patterns of steroid-RSA conjugate inhibition of 8G11-C6 reacting with antisteroid by ELISA was similar to that obtained with steroid inhibition RIA studies with the antisteroid. As similar ELISA results were obtained when the glucocorticoid receptor replaced the antisteroid, it was assumed that the same phenomenon occurred in this case as well. This was verified by the ability of 8G11-C6 immobilized on CNBr-Sepharose antimouse beads to deplete either free or [$^3$H]TA labeled receptor from rat liver cytosol. This again indicates that triamcinolone is not able to block the binding of 8G11-C6 to the receptor. Further evidence of interaction 8G11-C6 with [$^3$H]TA glucocorticoid receptor was obtained from the sucrose density studies.

The steroid-RSA inhibition studies demonstrate that 8G11-C6 is specific for the glucocorticoid receptor rather than other steroid receptors such as estrogen. This shows that the specificity of the receptor isolated is dependent on the ligand used for immunization and can be used in place of purified glucocorticoid receptor to isolate monoclonal antibodies. These results also show that 8G11-C6 could be used as an immunochemical to prepare an affinity column to purify the glucocorticoid receptor. Such an affinity column will have one advantage of being specific for the glucocorticoid receptor and not other steroid binding proteins. As the binding of triamcinolone does not affect the binding of 8G11-C6 to the receptor, the glucocorticoid receptor can be radiolabeled with [$^3$H]TA and its binding and elution profiles monitored. Furthermore, the sucrose density studies demonstrate that G11-C6 has a low affinity for the glucocorticoid receptor, it will enable the receptor to be eluted readily from the affinity column thus increasing the yield of undenatured receptor. In fact, the steroid RSA conjugate could be used to elute the receptor from such a column. 8G11-C6 together with other antiidiotypic antibodies that cross-react with the glucocorticoid receptor may be used as probes instead of radiolabeled ligands to identify and characterize the structure and function of the receptor.

The strategy described here provides a powerful route to anti-receptor antibodies which are likely to be directed at determinants associated with the combining sites of the receptor. The antibodies may be obtained in large quantity by culturing hybridoma cells by conventional in vitro or in vivo methods which are well known in the art. As in previous findings (1), purified receptor is not required for immunization; in fact, these antidiotypic antibodies presumably, can be used to isolate receptor. Furthermore, this invention is also applicable to receptors for other pharmacologically active, low molecular weight molecules, regulatory macromolecules such as lymphokines, and infectious agents such as viruses. Anti-receptor antibodies prepared with the invention may be useful in prevention and treatment of diseases. In particular, anti-receptor antibodies may be useful as substitutes for pharmacologically active substances such as interferon, interleukin 2, other lymphokines and in vaccines as substitutes for infectious agents. Immunity, to infectious agents such as viruses may be induced with antireceptor antibodies. Anti-receptor antibodies may also be useful as cytotoxic reagents for killing tumor cells, as well as normal cells of the body that may prevent acceptance of transplants. The invention can also be used to determine if a structure is a ligand for an unknown receptor. It is also possible that receptors isolated with antidiotypic antibodies of this invention may themselves be used as therapeutic agents in the future.

The examples which follow are set forth to aid in an understanding of the invention but are not intended to, and should not be construed to, limit in any way the invention as set forth in the claims which follow thereafter.

EXAMPLES

EXAMPLE 1

Synthesis of the BisQ-BSA Conjugate

All chemical reagents in this Example and in Examples 5 and 7 may be obtained from Aldrich Chem. Co., Milwaukee, Wis., unless otherwise indicated.

I. o-Hydroxy-N,N-dimethylbenzylamine (I)

30.5 g (0.25 mole) salicylaldehyde was mixed with 100 ml of a solution of 25 ug (0.53 mole) of dimethylamine in methanol cooled to 0.9C. After 24 hrs at room temperature in a stoppered flask, 1 g of 10% palladium on charcoal was added and the mixture hydrogenated at atmospheric pressure. The reaction was complete after 5600 ml of hydrogen was taken up. The catalyst was removed by filtration, the solvent removed in vacuo and the colorless oil distilling at 96°-98° C. at 10 mm collected Yield=30 g. For characterization, a portion of the product was allowed to react with methyl iodide in ethanol to yield the crystalline quaternary iodide; m.p. 169°-7° C. as found by Stedman (22).

II. 4-Hydroxy-3,3'bis-(α-dimethylamino)azotoluene (II)

15 g (0.1 mole) of m-(α-dimethylamino)toluidine (23) in 100 ml of 3.8 N HCl was diazotized with stirring at 0°-14° C. with 6.9 g (0.1 mole) of sodium nitrate in 25 ml water. The cold diazonium salt solution (with crushed ice in the dropping funnel) was added over a period of 40 min to a stirred mixture of 15.2 9 (0.1 mole) of I and 180 ml 20% $Na_2CO_3$ in water cooled at 0°-14° C. Stirring was continued for 5 hrs allowing the temperature to rise about 15° C. Final pH=9. The reaction mixture was acidified with concentrated HCl to pH 3 and extracted with ethyl ether. To the water layer was added, with stirring, enough 20% NaOH to raise the pH to 8.4. The precipitate was recovered by filtration, dried in a desiccator and recrystallized from n-hexane. Yield=7.4 g orange needles, m.p. 112°-3° C.

Anal. calcd. for $C_{18}H_2N_4O$: C=69 2, H=7.7, N=17.9. Found: C =69.1, H =8.0, N =17.8.

III. 4-(2'-Hydroxyethyloxy)-3,3'-bis-(α-dimethylamino)azotoluene (III)

0.625 g (2 mmoles) of II, 0.56 g (0.5 ml) (9 mmoles) of ethylene glycol, 0.7 g (3.4 mmoles) of dicyclohexylcarbodiimide and 1 ml of dry acetonitrile were introduced into a glass tube with a Teflon sealing top (Pierce 29564). After flushing with nitrogen, the tube was heated on a ReactiTherm Heating Module (Pierce 18800) at 110° C. for 44 hrs. After cooling to room temperature, 15 ml of dioxane were added, and the crystalline precipitate removed by filtration. The filtrate was concentrated to dryness in vacuo. The residual oil was diluted with 4 ml of methanol and applied to four preparative TLC plates of $Al_2O_3$ (E. Merck, 1.5 mm, F 254) and developed with ethyl acetate-hexane 2:1. The bands with Rf 0.7 were scraped off and eluted with methanol to yield, after distillation in vacuo, 0.24 g of an orange viscous oil (III) which was used in the next step, i.e. succinylation. For characterization, 0.100 g of the product was dissolved in 3 ml methanol and quaternized with excess methyl iodide (2 ml) at room temperature in a closed tube for three days. After distillation of excess solvent, the residue was recrystallized from absolute ethanol; yield=0.096 g of red orange needles, m.p. 155°-6° C. Anal. calcd. for $C_{22}H_{34}N_4O_2I_2$: C=41.26, H=5.35, N=8.75, I=39.64. Found: C=41.16, H=5.43, N=8.63, I=39.80.

IV. 4(2'-Succinoyloxyethyloxy)-3,3'-bis-(α-trimethylammonium)azotoluene diiodide (IV)

0.178 g (0.5 mmoles) of III, 0.100 g (1.5 mmoles) of succinic anhydride, 4 ml dry pyridine and 2 ml dry dioxane in a glass pressure tube (as for III) were heated on the heating module at 80°-84° for 24 hrs. Intermittent mixing with a Vortex was required until the solid dissolved. The reaction mixture was transferred to a chromatographic column (2.5 cm diameter) containing Sephadex® LH 20 (80 cm bed) (Pharmacia Fine Chemicals, Piscataway, N.J.) and equilibrated with methanol. Methanol was also used for elution. The fractions that emerged from the column between 256-285 ml were collected and distilled in vacuo to yield 0.136 g of an orange viscous oil, the tertiary base used in the quaternization step. It was dissolved in 4 ml of anhydrous ethanol, to which 4.56 g (2 ml) methyl iodide was added and allowed to react 20 hrs at 37° in a stoppered flask. The bis quaternary salt precipitated as orange needles. It was collected by filtration, washed with 1 ml of ethanol, then an excess of ethyl ether and dried in vacuo. Yield=0.096 g, m.p. 175°-7°. It was crystallized from 3 ml of ethanol; m.p. 178°-9°.

Anal. calcd. for $C_{26}H_{38}N_4O_5I_2$: C=42.17, H=5.17, N=7.57, I=34.28. Found: C=41.90, H=5.35, N=7.46, I=34.35.

V. Preparation of the Immunizing Conjugate (BisQ-Bsa)

IV was linked to bovine serum albumin (and to rabbit serum albumin) by the mixed anhydride technique (24) as follows: 56 mg (0.076 mmole) of IV was dissolved in 3.8 ml of DMF. The solution was cooled in an ice salt bath and 20 microliters (15.6 mg, 0.084 mmole) of trinbutylamine was added, followed by 11 microliters (11.5 mg, 0.084 mmole) of isobutylchloroformate. The solution was allowed to stand for 30 min in the ice salt bath and was then added in one portion, with stirring, to a cold solution of 213 mg ($3.2\times10^{-3}$ mmole) of bovine serum albumin in 11.5 ml of water. The albumin solution had been adjusted to pH 9 with 0.01 N NaOH. The solution was kept in the cold bath for three hours; 0.01 N NaOH had to be added periodically to keep the pH near 9. Then the solution was dialyzed exhaustively in the cold against several changes of distilled water. The product was then lyophilized. Approximately 8 molecules of IV were then linked to the albumin carrier, as determined spectro-photometrically by measurement of the absorbance of 324 nm (max, 20,000).

EXAMPLE 2

Preparation of Monoclonal Anti-AChR Antibodies

BALB/cCr mice were immunized intraperitoneally (i.p.) with 0.1 ml of a solution of BisQ-BSA conjugate (1 mg/ml) (prepared as in Example 1) in complete Freund's adjuvant. Twenty-three days later, the mice were boosted i.p. with the same preparation. After 5 days, the spleen cells were collected and fused with a nonsecreting myeloma line (P3x63-Ag 8.653) (25) essentially by the protocol of Kohler and Milstein (17) as modified by Sharon et al. (18). Supernatants from hybridoma clones were obtained by a replica transfer technique (19) and screened for activity against BisQ-R.SA, rabbit anti-BisQ and AChR by an enzyme immunoassay (1), using peroxidase-labeled goat anti-mouse immunoglobulin as the second antibody.

TABLE IV

| Screening of hybridoma cells | |
|---|---|
| Specificity | Positive wells[1] |
| BisQ-RSA | 14.0% (67/480) |
| Anti-BisQ | 7.4% (55/741) |
| AChR[2] | 2.4% (22/933) |

[1] Numbers in parentheses represent numbers of positive wells per no. of wells assayed. Anti-BisQ is the specifically purified rabbit antibody used in ref. 1.
[2] Wells positive for AChR were also positive for anti-BisQ, that is, they were a subset of the wells positive for anti-BisQ activity. Purified *Torpedo californica* and rat muscle receptor preparations gave the same results.

EXAMPLE 3

Recovery and Binding Activity of Monoclonal Antibodies from Clone F8-D5

Positive wells identified in Example 2 were then s cloned by the procedure of limiting dilutions and several of the clones that produced antibody reactive with both anti-BisQ and Torpedo receptor were examined. The monoclonal anti-idiotypic antibodies produced by one of the clones, F8-D5, were obtained as an ammonium sulfate precipitate of the supernatant.

Wells of polystyrene plates (Corning) were then coated with 150 microliters of either 400 ng/ml purified rabbit anti-BisQ (1) in 0.1 M NaHCO$_3$, pH 9.3, or 3 g/ml purified Torpedo receptor in the same buffer. Coating was accomplished by incubating for 2 h at 37° C. After two washings with 0.01 M phosphate buffer:0.14 M NaCl, pH 7.2, containing 0.05% v/v Tween-20 (PBS-Tween), the wells were exposed to the various concentrations of F8-D5 in PBS-Tween. After incubation at 37° C. for 2h, the wells were washed three times with PBS-Tween and then filled with 200 microliters of 1:1,000 dilution in PBS-Tween of goat anti-mouse immunoglobulin labeled with horseradish -peroxidase (Sigma). After incubation at 37° C. for 1 h, the wells were washed three times with PBS-Tween. Peroxidase was assayed by incubation with o-phenylenediamine dihydrochloride (7 mg in 10 ml 0.1 M citrate-phosphate buffer, pH 4.8, containing 5 microliters of 30% H$_2$O$_2$) for 10 min. The reaction was stopped with 50 microliters per well of 4 M H$_2$SO$_4$ and the color read at 492 nm in a Multiskan Titertek apparatus. Values were corrected for a PBS blank which was never higher than 0.150. (The above conditions were not chosen for optimal sensitivity but for speed and convenience.)

As FIG. 2 illustrates, the antibody produced by this clone was able to bind AChR of Torpedo as well as specifically purified rabbit anti-BisQ (1). This property was retained by clones obtained after two subsequent subclonings by limiting dilution. No attempt can be made to relate the respective binding affinities because of the characteristics of enzyme immunoassay procedures, in general. For example, there is no way to ensure that the same number of determinant sites of receptor and of anti-BisQ adhere to the plastic wells.

EXAMPLE 4

Reciprocal Inhibition Studies

To confirm that the same monoclonal antibody bound receptor and anti-BisQ, reciprocal inhibition experiments were carried. This assay was carried out essentially as described in Example 3, except that incubation with F8-D5 and inhibitor Torpedo AChR) was conducted as follows. Two rows of six wells were used; one served as the control (a blank). PBS-Tween (110 microliters) was added to the first wells of each row; 100 microliters of PBS-Tween were added to the other wells. Then 15 microliters of a purified Torpedo AChR preparation (1.52 mg/ml) were added to the first well of each row. Fivefold serial dilutions were then made by transferring 25 microliters from the first well to the second, 25 microliters from the second to the third, and so on. Finally, 5 microliter portions of F8-D5 (2 g/ml) were added to one row of wells and 5 microliters of PBS to the other row, which served as a control for each of the concentrations of AChR used as inhibitor. Wells containing PBS only and PBS plus F8-D5 were also prepared. Incubation of the solutions was for 2 h at 37° C. The rest of the assay was conducted as described in Example 3.

As FIG. 3 illustrates, the binding to anti-BisQ of an (NH$_4$)$_2$SO$_4$-precipitated supernatant of F8-D5 was inhibited by Torpedo receptor. At the highest concentration of receptor used, 67% inhibition was observed; 50% inhibition occurred with about 8 micrograms of inhibitor in the conditions described. In experiments in which the amount of antibody was decreased fivefold to 2 micrograms per well, 50% inhibition occurred in the presence of 0.9 micrograms of Torpedo receptor. In a similarly designed series of experiments, 50% inhibition of the binding of F8-D5 to Torpedo receptor was accomplished with 3 micrograms of purified rabbit antiBisQ.

Furthermore, the binding of F8-D5 to Torpedo receptor could be inhibited by BisQ, 50% inhibition occurring at a concentration of $4 \times 10^{-5}$M. A similar concentration of BisQ caused 50% inhibition of the binding of F8-D5 to rabbit anti-BisQ. These results reinforce the conclusion that the specificity of F8-D5 is for determinants intimately associated with the combining sites of both the Torpedo receptor and rabbit anti-BisQ. With respect to the latter, this is consistent with a specificity for an idiotypic determinant.

EXAMPLE 5

Synthesis of the CPA-BSA conjugate

I. $N^6$(Carboxypentamethylene)adenosine (CPA)

287 mg (1 mmole) of 9-($\beta$-D-ribofuranosyl)-6-chloropurine, 262 mg (2.0 mmoles) of $\epsilon$-aminocaproic acid and 0.6 ml (5.0 mmoles) triethylamine were suspended in 3 ml of dimethylformamide. The suspension was warmed to 35° C. to dissolve most of the reactants and then allowed to stand for 96 hours at room temperature with stirring. It was then heated to 60° C. and kept at that temperature for 48 hours with stirring. The solution was concentrated to ¼ of its volume in vacuo and covered with 100 ml of ether, after which it was allowed to stand for 24 hours at 4° C. The ether layer was decanted, 15 ml of water was added to the residual oil, and the pH adjusted to 3.0 to yield a clear solution. The solution was concentrated to one-half volume in vacuo. Crystals appeared and the solution was allowed to stand for several days at 4° C. The crystals were collected and recrystallized from water to yield 75 mg of CPA. An additional 50 mg was recovered from mother liquors. The compound analyzed correctly for the monohydrate.

Calcd. C, 48.11; H, 6.35; N, 17.54 (C$_{16}$H$_{23}$O$_6$N$_5$·H$_2$O). Fd. C, 48.84; H, 6.35; N, 17.51.

II. Coupling of CPA to Bovine Serum Albumin (BSA)

CPA was first converted into the N-hydroxysuccinimide ester, as follows:

50 mg (0.131 mmoles) of CPA was dissolved in 2 ml of dry pyridine. Then 24 mg (0.210 mmoles) of N-hydroxysuccinimide was added. This was followed by 34 mg of N,N,-dicyclohexycarbodiimide in 1 ml of dry pyridine. The resulting solution was allowed to stand for 48 hours at room temperature. Crystals of the urea byproduct were separated from the pyridine solution by filtration. A portion of the filtrate containing 0.6 mmoles of the N-hydroxysuccinimide ester of CPA was added to 96 mg of BSA dissolved in 2 ml of water adjusted to pH 9.2. The pH dropped to 7.5 but was adjusted to 9.2 by the addition of a small amount of a saturated solution of $K_2CO_3$. After four hours of reaction, the reaction mixture was dialyzed exhaustively against water. By ultraviolet spectrophotometry, the conjugate was found to have about 10 moles of adenosine derivative per mole of BSA.

EXAMPLE 6

Preparation of Monoclonal Antibodies to Adenosine Receptors

Protocols for immunization and fusion were essentially identical to that described previously for BisQ in Example 2. Immunization was effected with the RSA conjugate, but the BSA conjugate is just as satisfactory. Screening was conducted with the BSA conjugate and with a specifically purified rabbit antibody raised by immunization with the BSA conjugate. Specifically purified antibody was prepared in a manner analogous to that described for anti-BisQ antibody (1) except that the immunoadsorbent was $N^6$-(carboxypentamethylene) adenosine linked to aminohexylsepharose (Pharmacia).

Monoclonal anti-idiotypic antibodies were obtained and were found to bind both rabbit anti-CPA and a preparation of adenosine receptor obtained from rat brain (20). The reaction with receptor could be inhibited by biologically active adenosine derivatives including $N^6$-cyclohexyladenosine.

EXAMPLE 7

Synthesis of the Triamcinolone (TA)-protein Conjugate

I. δ-ketohexanoic-N-hydroxysuccinimide ester 0.024 moles 4-acetylbutyric acid was stirred in approximately 60 ml dioxane. To this stirred solution was added a solution of 0.036 moles N-hydroxysuccinimide in dioxane. More dioxane was added until all of the N-hydroxyhemisuccinimide was in solution. Finally 0.025 moles of dicylohexylcarbodiimide in dioxane was added and the solution, in a total volume of 100 ml, stirred overnight. The insoluble dicyclohexylurea was removed by filtration and the filtrate concentrated by evaporation in a rotary evaporator. The product was extracted with 200 ml methylene chloride. After 5 washes with water to remove dioxane and unreacted N-hydroxy-succinimide, the methylene chloride extract was dried with solid magnesium sulfate and decolorized with norit A. The solids were removed by filtration through celite 545 and the filtrate was concentrated by rotary evaporation. The product was examined for the presence of the ester by TLC using an analytical silica gel TLC plate and eluting with 2% methanol in methylene chloride (v/v). The ester was identified by the Fe-hydroxamate test (27).

Purification of δ-ketohexanoic-N-hydroxysuccinimide ester

Approximately 9 g of the concentrate containing the ketohexanoicsuccinimide ester was chromatographed on a column containing 160 g Silica gel 60 in chloroform. After washing with 100 ml chloroform, the -ketohexanoic-hydroxysuccinimide ester was eluted with 3% methanol in chloroform (v/v). The first 250 ml were discarded after which 20 ml fractions were collected, until all the color was eluted from the column. The purity of δ-ketohexanoic-hydroxysuccinimide in the various fractions was then assessed by TLC as described above. The pure fractions were combined and evaporated to dryness.

II. Coupling of δ-ketohexanoic-hydroxysuccinimide ester to triamcinolone

Triamcinolone (0.8 g) and 0.9 g of δ-ketohexanoic hydroxysuccinimide ester were suspended in 16 ml dioxane with stirring, followed by careful addition of 0.3 ml perchloric acid. Stirring was allowed to continue overnight at room temperature yielding a clear solution. The reaction was terminated by neutralizing with $Na_2CO_3$, and the product extracted with 100 ml methylene chloride. After washing with 200 ml $H_2O$, the upper water phase was discarded and the lower methylene chloride phase was dried over solid $MgSO_4$. After filtration and evaporation to dryness, the product was chromatographed by TLC using 10% methanol in chloroform as the developing solvent. The product was detected as an ester as before (27) and distinguished from the starting material by its strong UV activity.

Purification of triamcinolone δ-ketohexanoic-hydroxysuccinimide ester

A chloroform solution of the product was passed through a silica gel 60 column (100 g) that had been equilibrated with chloroform. Development was with 7.5% methanol in chloroform, using a slow flow rate. Ten milliliter fractions were collected and examined for product by TLC chromatography on silica gel 60 using 10% methanol in chloroform as solvent. The fractions containing the triamcinolone δ-ketohexanoic-hydroxycontaining succinimide ester were combined, concentrated by rotary evaporation and purified further by HPLC, using a silica column of 21.2 mm × 25 cm dimensions. MethaZOBOX nol 3% (v/v) in chloroform at a flow rate of 16 ml/min produced 2 major peaks which were concentrated by rotary evaporation. Pure steroid ester was identified in the second peak by TLC chromatography as was described above.

III. Coupling of triamacinolone δ-ketohexanoic hydroxysuccinimide ester to BSA, RSA or thyroglobulin A solution of $1.4 \times 10^{-4}$ moles of the steroid ester dissolved in 2 ml of tetrahydrofuran was added dropwise to a solution of $2.8 \times 10^{-6}$ moles of protein dissolved in 5 ml 0.2 M $Na_2CO_3/NaHCO_3$ buffer adjusted to pH 8.0. Additional tetrahydrofuran had to be added to clarify the solution. After standing overnight at 4° C., the solution was dialyzed against several changes of distilled water. A white precipitate formed, most of which was redissolved by dropwise addition of 0.2M Na$_2$CO$_3$. Additional distilled H$_2$O was added to bring the volume to 35 ml and the suspension was centrifuged at 4° C. to remove denatured protein. The amount bound was calculated from the E$_{max}$ of the steroid ester, which was previously determined to be 1.2×10$^4$ at E$_{max}$ 243 nm. The results were 18–23 units steroid/mole RSA, 16 units steroid/mole thyroglobulin.

The other steroid conjugates namely 17$\beta$-estradio-RSA, testosterone-RSA, cortisone-RSA and deoxycortisone-RSA were previously synthesized (28, 29).

EXAMPLE 8

Preparation and isolation of specifically purified polyclonal anti-steroid from rabbit serum (a) Immunization protocol New Zealand white rabbits were immunized by multiple intradermal injections of a total of 1 ml of triamcinolone-BSA (2 mg/ml) emulsified with an equal volume of complete Freunds adjuvant or saline. Booster injections were given three weeks later and then at monthly intervals. Animals were bled bi-weekly from the ear vein and the sera stored at 4° C. until required.

(b) Affinity chromatography of the anti-steroid-preparation of AH-Sepharose 4B-triamcinolone column AH-Sepharose 4B (1 g) was suspended in 100 ml of 0.5N NaCl. After 15 min, the slurry was filtered on a Buchner funnel and washed with 250 ml of 0.5N NaCl and then with 250 ml water. The gel was transferred to a centrifuge tube and washed five times with 10 ml 0.2M NaHCO$_3$ pH 8.15. After the last wash, the supernatant was discarded and an equal volume of 0.2M NaHCO$_3$ pH 8.15, was added followed by 58.6 mg triamcinolone N-hydroxysuccinimide ester in 3–5 ml of tetrahydrofuran. The suspension was mixed overnight at 4° C., followed by centrifugation of the gel and washing with a methanol/H$_2$O solution (1:1), distilled H$_2$O and equilibranol with PBS. The gel was poured into a 10 cc Luerlock plastic syringe to obtain about a 4 ml bed volume. Storage was at 4° C.

(c) Purification of the polyclonal anti-steroid antibody

Thirty to 40 ml of serum obtain part (a) of this example were passed slowly (±3.5 ml/hr) through the AH-Sepharose 4B-triamcinolone column prepared according to (b) above. After washing with PBS to remove all unbound protein, the antibody was eluted with 0.2M glycine pH 2.2 or 2.8. The eluate was dialyzed against 2 liters, 0.01M PBS buffer pH 7.4 and the buffer changed at least 4 times before concentrating by vacuum dialysis at 4° C.

(d) Preparation of Fab fragments

The method of Porter (30) was used whereby 5.5 ml of affinity purified anti-steroid antibody (20 mg) obtained in (c), above, was dialyzed against 0.1 M potassium phosphate buffer pH 7.0 containing 0.45% NaCl for 2 hrs at 4° C. To the dialysate was added 0.1 M dithiothreitol (DTT) (15 microliters), EDTA (2 mg), and 0.2 mg mercuripapain (5 microliters) and the solution was incubated overnight at 37° C. It was then dialyzed against 4 liters distilled H$_2$O for 3 hrs and then against 1 liter of PBS for 2 hrs and then applied to a Sephadex G100 column (1×5×90 cm) and eluted (±5ml/hr) with 0.01M PBS pH 7.4. One ml fractions were collected Fractions 53–79 were combined and examined at 280 nm for protein content. Undigested IgG and Fc fragments were removed by passage through a protein A Sepharose column (5 ml bed volume); unbound Fab was eluted with 0.01 M PBS pH 7.4. The eluate was concentrated by vacuum dialysis.

EXAMPLE 9

Preparation and isolation of monoclonal anti-idiotypic antibody

Two female Balb/c mice were immunized i.p. with 0.1 ml of a 1 mg/ml solution of triamcinolone-thyroglobulin conjugate in complete Freunds adjuvant. Three weeks later the mice were boosted i.p. with the same preparation. After another 4 week interval, the animals were boosted a second time i.p. with the same preparation. Four days after the final immunization, one of the mice was splenectomized. 2×10$^8$ spleen cells were fused with 2×10$^7$ cells of a non-secreting myeloma line (P3×63-Ag 8.653) (31) according to the procedure of Kohler and Milstein (17) as modified by Sharon et al. (18). Supernatants from the hybridomas were obtained by a replica transfer technique (32) and screened for anti-idiotypic activity by ELISA. Monoclonal antibody-producing hybridomas were obtained by cloning the cells of the cultures of interest on soft agar or by using a micromanipulation technique (33). The class and subclass of the heavy chain of the monoclonal antibodies were determined by Ouchterlony and by ELISA using antimouse Ig class and subclass antisera as typing serum or to coat microtitre plates. The clones of interest were expanded by growing them in 75 cm$^2$ T-flasks. The antibodies in the culture medium were purified by precipitation in 50% saturated (NH$_4$)$_2$SO$_4$.

Enzyme-linked immunosorbent assay

The presence of anti-idiotypic antibodies in the hybridoma culture medium were assayed by a double antibody sandwich ELISA. Polystyrene microplates (Corning 25855) were coated by adding 200 microliters of 50 ng/ml affinity purified rabbit anti-steroid FAB fragments in 0.1 M NaHCO$_3$, pH 9.3, to the wells and incubating overnight at 4° C. After washing twice with 0.01M phosphate buffer - 0.14M NaCl, pH 7.4, containing 0.05% Tween (PBS-tween), the culture medium from the hybridomas was added and incubated at 37° C. for 2 hrs. The wells were washed three times with PBS-tween and 200 microliters of 1:3,000 dilution in PBS-tween of goat anti-mouse IgM-IgG horseradish peroxidase (Tago) was added. After incubating 1 hr at 37° C., the wells were washed three times with PBS-tween and 200 microliters substrate (7 mg o-phenylenediamine dichloride in 10 ml 0.1 M citrate-phosphate buffer, pH 4.8 containing 5 microliters of 30% H$_2$O$_2$) was added. Depending on the intensity of the color, the reaction was stopped after 5–10 min by the addition of 50 microliters 8N H$_2$SO$_4$ and the OD determined (Titretek) at 492 nm.

EXAMPLE 10

Cytosol Preparation of the glucocorticoid receptor

Four to 6 days after 150–200g Sprague-Dawley male rats were adrenalectomized, they were anaesthesized with ether and the livers perfused in situ through the portal vein with 50 ml of cold saline. The livers were then removed, homogenized with a Teflon-glass homogenizer in 1.1 volume of 10 mM HEPES, containing 50 mM NaCl, 1 mM Na$_2$ EDTA, 1 mM dithiothreitol (DTT) and 10% glycerol, pH 7.6, and centrifuged for 1 hr at 250,000 g at 4° C. The upper fatty layer was discarded. The supernatant was either frozen immediately in liquid-nitrogen and used for assays or labeled by incubating with 75 nM [$^3$H] triamcinolone acetonide for 2 hrs at 4° C. Unbound steroid was removed with 5% dextran-coated charcoal. The [$^3$H]TA glucocorticoid receptor was partially purified by the method described by Gametchu & Harrison (9), the only modification being that the phosphocellulose was omitted from the first purification step.

EXAMPLE 11

Depletion assay using rabbit or goat anti-mouse Sepharose-4B to which the putative mouse anti-receptor antibody was bound (a) Preparation of the Sepharose-4B immunoadsorbent Affinity chromatography-purified rabbit or goat anti-mouse IgM was coupled to cyanogen bromide activated Sepharose-4B as described by Westphal et al. (35) and in the Affinity Chromatography Handbook of Pharmacia. Cyanogen bromide (CNBr)-activated Sepharose (500 mg) was swollen in 1 mM HCl and washed on a sintered funnel with 1 mM HCl (200 ml). The gel was washed twice with coupling buffer (0.25 M NaHCO$_3$ containing 0.5M NaCl pH 8.5) and suspended immediately in a (4 mg/3 ml) affinity purified anti-mouse IgM solution. The suspension was mixed gently by rotating either for 2 hrs at room temperature or overnight at 4° C. The mixture was then centrifuged in a clinical centrifuge and the gel sediment reacted with 1 M ethanolamine pH 8.2 either for 1 hr at room temperature or overnight at 4° C. It was then washed with 15 ml 0.1 M acetate buffer containing 1 M NaCl, pH 4.0, followed by 0.1 M borate buffer pH 8.0, and then with PBS several times and suspended in 3 volumes of PBS.

(b) Assay of supernatants for receptor binding activity

Antibody containing culture medium (1-3.5 ml) was mixed with 125 microliters of anti-mouse-Sepharose-4B beads overnight at 4° C. The AM-Sepharose-4B beads were centrifuged down and washed 3 times with 2 ml PBS. Rat liver supernatant (300 microliters) containing 0.09-0.18 pmoles of receptor was added and mixed for 2 hrs at 4° C. The gel was centrifuged down and 200 microliters of the supernatant was assayed for glucocorticoid receptor after adding 25 microliters of 25nM [$^3$H]TA and incubating it at 4° C. for 2 hrs. Unbound [$^3$H]TA was removed by adding 100 micrograms of 5% charcoal/dextran and allowing it to stand at 4° C. for 5 mins. Cold PBS (1 ml) was added and after 5 mins the charcoal/dextran was centrifuged down. The supernatant wa assayed in a scintillation counter.

EXAMPLE 12

Sucrose density gradient experiments

The glucocorticoid receptor was radiolabeled by incubating 0.5 ml rat liver cytosol with 10nM [$^3$H]TA for 2 hrs at 4° C. Five percent charcoal/dextran (0.25 ml) was added and the suspension allowed to stand for 10 min at 4° C. After centrifugation, 4° C., either 50 microliters of [$^3$H]TA radiolabeled cytosol (0.16 p moles) was incubated together with 190 microliters of PBS at 4° C., or 50 microliters of [$^3$H]TA radiolabeled cytosol together with 190 microliters of 50% (NH$_4$)$_2$SO$_4$ precipitated 8G11C6 (9.4 mg/ml). To the incubates add 100 microliters of affinity purified goat anti-mouse-IgM (3.4 microliters/ml) or PBS was added and the mixture incubated for a further 2 hrs at 4° C.

The incubation mixture (240 microliters) was layered on 4.4 ml of a continuous 5-20% sucrose density, gradient containing 10 mM Tris HCl buffer, 1 mM EDTA and 0.4 M KCl. The gradient was prepared on a 0.2 ml 40% sucrose cushion. Centrifugation was in a Beckman SW55 rotor at 300,000 ×g for 3 hrs. Two to 3 drop fractions were obtained by puncturing the bottom of the tube.

REFERENCES

1. Wassermann, N. H. et al., Proc. Natn. Acad. Sci. U.S.A. 79:4810-4814 (1982).
2. Schecther, Y., Maron, R., Elias, D. & Cohen, I. R., Science 216:542-544 (1982).
3. Tzartos, S. J., Seybold, M .E. & Lindstrom, J. M., Proc. Natn. Acad. Sci. U.S.A. 79:188-192 (1982).
4. Fulpius, B. W., Lefvert, A. K., Cuenoud, S. & Mourey, A., Ann. N.Y. Acad. Sci. 377:307 (1981).
5. Rees-Smith, B. & Hall, R., Lancet ii, 427 (1974).
6. Jensen, E. V. & Green, G. L., Dev. Endocrinol. 12:317-333 (1981).
7. Yavin, E., Horiz, Biochem. Biophys., 6(Hormone Receptors):67-81 (1982).
8. Waldor, M. K. et al., Natn. Acad Sci. U.S.A. 80:2713-2717 (1983).
9. Bartels, E., Wassermann, N. H. & Erlanger, B. F., Proc. natn. Acad. Sci. U.S.A. 68:1820-1823 (1971).
10. Wassermann, N. H., Bartels, E. & Erlanger, B. F., Proc. Natn. Acad. Sci. U.S.A. 68:256-259 (1979).
11. Heidmann, T. & Changeux, J. P., A. Rev. Biochem. 47:317-357 (1978).
12. Ouidin, Y. & Michael, M., C.r. hebd. Seanc. Acad. Sci., Paris 257:805-808 (1963).
13. Kunkel, H. G., Mannick, M. & Williams, R. C., Science 140:1218-1219 (1963).
14. Farid, N. R. et al., J. Cell. Biochem. 19(4):305-313 (1982).
15. Jerne, N. K., Annls. Inst. Pasteur, Paris, 125C:373-389 (1974).
16. Geha, R. S., J. Immun. 129:139-144 (1982).
17. Koehler, G. & Milstein, C., Nature 256:495-497 (1975).
18. Sharon, J., Morrison, S. L. & Kabat, E. A., Proc. Natn. Acad. Sci. U.S.A. 76:1420-1424 (1979).
19. Cleveland, W. L., Sarangarajan, R. & Erlanger, B. F., J. Immunol. Meth. (submitted).
20. Gavish, M., Goodman; R. R. & Snyder, S. H., Science 215:1633-1635 (1982).
21. Binion, S. & Rodkey, L. S., J.Exp. Med. 156:860-872 (1982).
22. Stedman, E., J. Chem. Soc., 1902-1907 (1927).
23. Wassermann, N. H. & Erlanger, B. F., Chem. Biol. Interactions 36:251-258 (1981).
24. Erlanger, B. F., Pharmacol. Rev. 25:271-280 (1973).
25. Kearney, J. F., Radbruch, B. L. & Rajewsky, K., J. Immun 123:1548-1550 (1979).
26. Borrebaeck, C. A. K., Acta Chemica Scand. B37:647-648.
27. Randerath, K., in Thin Layer Chromatography, p. 203, Verlag Chemie, Academic Press (1963).
28. Erlanger, B. F., Borek, F., Beiser, S. M. and Lieberman, S., J. Biol. Chem. 228:713-727 (1957).
29. Erlanger, B. F., Borek, F., Beiser, S. M. and Lieberman, S., J. Biol. Chem. 234: 1090-1094 (1959).

30. Porter, Biochem. J. 73:119 (1959).
31. Kewney, J. F., Radbruch, B. L. and Rajewsky, K., J. Immunol. 123:1548–1550(1979).
32. Cleveland, W. L., Sarangarajan, R. and Erlanger, B. F., J. Immun. Meth. (in press).
33. (Missing No. 26 from references cited in Dr. Edelman's manuscript).
34. Gametchu, B. and Harrison, R. W., Endocrinol. 114:274–279 (1984).
35. Westphal, H. M., Moldenhauer, G. and Beato, M., EMBO 1:1467–1471 (1982).
36. Cleveland, W. L., Wassermann, N. H., Sarangarajan, R., Penn, A. S. and Erlanger, B. F., Nature 305:56–57 (1983).
37. Sege, K. and Peterson, P. A. Proc. Natl. Acad. Sci. USA 75:2443–2447 (1978).
38. Schreiber, A. B., Courand, P. O., Andre, C., Vray, B. and Strosberg, A. D. Proc. Natl. Acad. Sci. USA 77:7385–7389 (1980).
39 Homcy, C. J., Rockson, S. G. and Haber, E. J. Clin. Invest. 69:1147–1153 (1982).
40. Marasco, W. A. and Becker, E. L. J. Immunol. 128:963–968 (1982).
41. Nepom, J. T., Weiner, H. L., Dichter, M. A. et al. J. Exp. Med. 155–163 (1982).
42. Schreiber, M., Fogelfield, L. F., Souroujon, M. C., Kohn, F. and Fuchs, S. Life Sci. 33:1519–1529 (1983).

What is claimed is:

1. An isolated monoclonal, auto-anti-idiotypic antibody capable of binding to an adenosine receptor produced according to the method comprising:
   (a) contacting lymphoid cells of an animal under suitable conditions with an effective auto-anti-idiotypic antibody-raising amount of $N^6$-carboxypentamethylene adenosine conjugated to a protein, so that the lymphoid cells produce auto-anti-idiotypic antibodies thereto,
   (b) collecting the antibody-producing lymphoid cells at least three days after contacting them with the $N^6$-carboxypentamethylene adenosine conjugate,
   (c) fusing the antibody-producing lymphoid cells so collected with appropriate myeloma cells to produce a series of hybridoma cells, each of which produces a monoclonal antibody,
   (d) screening under suitable conditions the series of hybridoma cells so produced to identify a hybridoma cell which secretes a monoclonal antibody capable of binding to both the adenosine receptor and an antibody directed to $N^6$-carboxypentamethylene adenosine,
   (e) separately culturing the hybridoma cell so identified in an appropriate medium, and
   (f) separately recovering under suitable conditions the monoclonal, auto-anti-idiotypic antibody produced by the hybridoma cell.

* * * * *